(12) United States Patent
Singh

(10) Patent No.: US 9,717,626 B2
(45) Date of Patent: Aug. 1, 2017

(54) GASTRODUODENAL BALLOON TUBES AND METHODS FOR USE IN LOCALIZED HYPOTHERMIA

(71) Applicant: Mayo Foundation for Medical Education and Research, Rochester, MN (US)

(72) Inventor: Vijay P. Singh, Pittsburgh, PA (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 973 days.

(21) Appl. No.: 13/972,123

(22) Filed: Aug. 21, 2013

(65) Prior Publication Data

US 2013/0338741 A1 Dec. 19, 2013

Related U.S. Application Data

(62) Division of application No. 12/490,671, filed on Jun. 24, 2009, now Pat. No. 8,529,612.

(60) Provisional application No. 61/075,177, filed on Jun. 24, 2008.

(51) Int. Cl.
| | |
|---|---|
| *A61F 7/12* | (2006.01) |
| *A61F 7/10* | (2006.01) |
| *A61M 25/00* | (2006.01) |
| *A61M 25/10* | (2013.01) |
| *A61B 90/00* | (2016.01) |

(52) U.S. Cl.
CPC ......... *A61F 7/123* (2013.01); *A61M 25/1011* (2013.01); *A61B 90/39* (2016.02); *A61F 7/10* (2013.01); *A61M 25/007* (2013.01); *A61M 25/1002* (2013.01); *A61M 2025/0034* (2013.01)

(58) Field of Classification Search
CPC combination set(s) only.
See application file for complete search history.

(56) References Cited

U.S. PATENT DOCUMENTS

| | | | |
|---|---|---|---|
| 3,254,652 A | 6/1966 | Smith et al. | |
| 3,460,538 A | 8/1969 | Armstrong | |
| 3,768,484 A | 10/1973 | Gawura | |
| 4,543,089 A * | 9/1985 | Moss | A61J 15/0015 604/43 |
| 5,007,437 A * | 4/1991 | Sterzer | A61B 18/18 604/915 |
| 5,151,100 A | 9/1992 | Abele et al. | |
| 6,427,089 B1 | 7/2002 | Knowlton | |
| 6,558,412 B2 | 5/2003 | Dobak, III | |

(Continued)

FOREIGN PATENT DOCUMENTS

| | | | | |
|---|---|---|---|---|
| SU | 1378835 | * | 3/1988 | ............... A61F 7/12 |
| SU | 1378835 A1 | | 3/1988 | |

OTHER PUBLICATIONS

Patiutko et al. "Ways of improving results of gastro-pancreatoduodenal resection in tumors of the bilio-pancreatoduodenal area" Khirurgiia (Mosk). 1995;(3):26-9.*

(Continued)

*Primary Examiner* — Joseph Stoklosa
*Assistant Examiner* — Adam Avigan
(74) *Attorney, Agent, or Firm* — Mueting, Raasch & Gebhardt, P.A.

(57) ABSTRACT

Materials and methods for producing localized hypothermia in a patient (e.g., for treatment of acute pancreatitis and pancreatic cancer).

18 Claims, 10 Drawing Sheets

(56) References Cited

U.S. PATENT DOCUMENTS

| | | | |
|---|---|---|---|
| 6,589,271 | B1 | 7/2003 | Tzeng et al. |
| 6,726,708 | B2 | 4/2004 | Lasheras |
| 6,818,011 | B2 | 11/2004 | Dobak, III |
| 7,063,718 | B2 | 6/2006 | Dobak, III |
| 7,077,825 | B1 | 7/2006 | Stull |
| 7,758,623 | B2 | 7/2010 | Dzeng et al. |
| 8,231,664 | B2 | 7/2012 | Kulstad et al. |
| 8,361,132 | B2 | 1/2013 | Arad |
| 2005/0240250 | A1 | 10/2005 | Dobak, III |

OTHER PUBLICATIONS

Tenner. "Initial management of acute pancreatitis: critical issues during the first 72 hours," American Journal of Gastroenterology. 2004; 99:2489-2494.*
Bai et al., "Meta-analysis: allopurinol in the prevention of postendoscopic retrograde cholangiopancreatography pancreatits," Alimentary Pharmacology & Therapeutics, 2008;28:557-564.
Buchan, "Gastric freezing in the rat," Gut, 1965;6(5):494-499.
Büchler et al., "Gabexate Mesilate in Human Acute Pancreatitis," Gastroenterology, 1993;104:1165-1170.
Cho et al., "Endoscopic cryotherapy for the management of gastric antral vascular ectasia," Gastrointest. Endosc., 2008;68(5):895-902.
Everhart et al., "Burden of Digestive Diseases in the United States Part I: Overall and Upper Gastrointestinal Diseases," Gastroenterology, 2009;136:376-386.
Fischer et al., "Phosphatidylinositol 3-kinase facilitates bile acid-induced $Ca^{2+}$ responses in pancreatic acinar cells," Am. J. Physiol. Gastrointest. Liver Physiol., 2007;292:G875-886.
Funihashi, "Identification and characterization of a cathepsin B-like protease in Physarum sclerotium," Int. J. Biochem. Cell Biol., 2002;34(10):1308-1316.
Gaggiotti et al., "Adjustable Totally Implantable Intragastric Prosthesis (ATIIP)—Endogast® for Treatment of Morbid Obesity: One year follow-up of a Multicenter Prospective Clinical Survey," Obes. Surg., 2007;17(7):949-956.
Genco et al., "BioEnterics® Intragstric Balloon (BIB®): a short-term, double-blind, randomised, controlled, crossover study on weight reduction in morbidly obese patients," Int. J. Obes. (Lond.), 2006;30:129-133.
Gukovskaya et al., "Cell death in pancreatitis: effects of alcohol," J. Gastro. Hepa., 2006;21:S10-S13.
Gukovskaya et al., "Ethanol Metabolism and Transcription Factor Activation in Pancreatic Acinar Cells in Rats," Gastroenterology, 2002;122:106-118.
Hagiwara et al., "Changes in cell culture termperature alter release of inflammatory mediators in murine macrophagic RAW264.7 cells," Inflamm. Res., 2007;56:797-303.
Johnson et al., "Double blind, randomised, placebo controlled study of a platelet activating factor antagonist, lexipafant, in the treatment and prevention of organ failure in predicted severe acute pancreatitis," Gut, 2001;48:62-69.
Lu et al., "Alcohols enhance caerulein-induced zymogen activation in pancreatic acinar cells," Am. J. Physiol. Gastrointest. Liver Physiol., 2002;282:G501-G507.
Lunding et al., "Pressure-induced gastric accommodation studied with a new distension paradigm. Abnormally low accommodation rate in patients with functional dyspepsia," Scand. J. Gastroenterol., 2006;41:544-552.
Matsuoka et al., "Effects of Moderate Hypothermia on Proinflammatory Cytokine Production in a Rat Model of Caerulein-Induced Pancreatitis," Pancreas, 2003;26(1):e12-e17.
McFarland et al., "The clinical place of gastric hypothermia," Ann. R. Coll. Surg. Engl., 1968; delivered at the Royal College of Surgeons of England on Apr. 27, 1967;42(3):182-205.
Melnyk et al., "Gastric Freezing in Dogs," Ann. Surg., 1965;162:135-144.
Mundt et al., "Fundal dysaccommodation in functional dyspepsia: head-to-head comparison between the barostat and three-dimensional ultrasonographic technique," Gut, 2006;55:1725-1730.
Mutinga et al., "Does Mortality Occur Early or Late in Acute Pancreatitis? " Int. J. Pancreatol., 2002;28(2):91-95.
Nabseth et al., "Studies on the effect of intragastric cooling on acute experimental pancreatitis," Surgery, 1960;47(4):542-547.
Patiutko et al., "Ways of improving results of gastro-pancreatoduodenal resection in tumors of the bilio-pancreatoduodenal area," Khirurgila (Mosk), 1995;(3):26-29 (abstract only).
Preuss et al., "Pancreatic changes in cases of death due to hypothermia," Forensic Science International, 2007;166:194-198.
Rakonczay et al., "The Effects of Hypo- and Hypothermic Pretreatment on Sodium Taurocholate-Induced Acute Pancreatitis in Rats," Pancreas, 2002;24(1):83-89.
Ransom et al., "Long Peritoneal Lavage Decreases Pancreatic Sepsis in Acute Pancreatitis," Ann. Surg., 1990;211(6):708-716.
Renner et al., "Death Due to Acute Pancreatitis. A Retrospective Analysis of 405 Autopsy Cases," Digestive Diseases and Sciences, 1985,30(10):1005-1018.
Roddenberry et al., "Hypothermia in the Treatment of Acute Pancreatitis," J. Am. Med. Assoc., 1967;201(11):825-827.
Sahani et al., "Autoimmune Pancreatitis: Disease Evolution, Staging, Response Assessment, and CT Features that Predict Response to Corticosteriod Therapy," Radiology, 2009;250(1):118-129.
Schröder et al., "Pancreatic Resection Versus Peritoneal Lavage in Acute Necrotizing Pancreatitis. A Prospective Randomized Trial," Ann. Surg., 1991;214(6):663-666.
Singh et al., "Phosphatidylinositol 3-kinase-dependent activation of trypsinogen modulates the severity of acute pancreatitis," J. Clinical Invest., 2001;108(9):1387-1395.
Singh et al., "Serine Protease Inhibitor Causes F-Actin Redistribution and Inhibition of Calcium-Mediated Secretion in Pancreatic Acini," Gasteroenterology, 2001;120:1818-1827.
Singh et al., Protease-activated receptor-2 protects against pancreatitis by stimulating exocrine secretion, Gut, 2007;56:958-964.
Singh et al., "Src-mediated Cortactin Phosphorylation Regulates Actin Localization and Injurious Blebbing in Acinar Cells," Mol. Biol. Cell, 2008;19:2339-2347.
Singh et al., "Nelfinavir/ritonavir Reduces acinar injury but not inflammation during mouse caerulein pancreatitis;" Am. J. Physiol. Gastrointest. Liver Physiol., 2009;296:G1040-G1046.
Sipos et al., "Temperature-dependent activation of trypsin by calcium," Biochem. Biophys. Res. Commun., 1968;31(4):522-527.
Stiff et al., "Hypothermia and acute pancreatitis: myth or reality?" J.Royal Soc. Med., 2003;96(5):228-229.
Symbas et al., "Influence of Hypothermia on Pancreatic Function," Ann. Surg., 1961;154(4):509-515.
Tenner, "Initial Management of Acute Pancreatitis: Critical Issues During the First 72 hours," Am. J. Gastro., 2004;99:2489-2494.
Thrower et al., "Molecular basis for pancreatitis," Curr. Opin. Gastroenterology, 2008;24:580-585.
Van Acker et al. "Cathepsin B inhibition prevents trypsinogen activation and reduces pancreatitis severity," Am. J. Phys. Gastrointest. Liver Physiol., 2002; 283:G794-G800.
Wels et al., "Hypothermia in acute hemorrhagic pancreatitis," Arch. Surg., 1962;85:817-821.
White et al., "Problems and Complications of Gastric Freezing," Annals of Surgery, 1964;159(5):765-768.
Yokoyama et al., "Intense PET Signal in the Degenerative Necrosis Superimposed on Chronic Pancreatitis," Pancreas, 2005;31:192-194.

* cited by examiner

GASTRODUODENAL BALLOON TUBES AND METHODS FOR USE IN LOCALIZED HYPOTHERMIA

CROSS-REFERENCE TO RELATED APPLICATIONS

This application is a divisional application of U.S. patent application Ser. No. 12/490,671, filed Jun. 24, 2009, and titled GASTRODUODENAL BALLOON TUBES AND METHODS FOR USE IN LOCALIZED HYPOTHERMIA, which claims benefit of priority from U.S. Provisional Application Ser. No. 61/075,177, filed on Jun. 24, 2008, each of which is hereby incorporated by reference in its entirety.

TECHNICAL FIELD

This document relates to materials and methods for using localized hypothermia to treat disorders such as acute pancreatitis and pancreatic cancer.

BACKGROUND

The pancreas is a digestive and endocrine gland that produces several important hormones, including insulin, glucagon, and somatostatin. The pancreas also secretes digestive enzymes that pass into the small intestine and assist in breakdown of carbohydrates, protein, and fat in the digestive system. The pancreas is in a retroperitoneal position in the abdomen. The stomach lies anterior to the pancreas and covers most of its anterior surface, while the superior, medial and inferior surfaces of the pancreas are surrounded by the first, second, and third portions of the duodenum.

Acute pancreatitis is a rapid-onset inflammation of the pancreas. This disease typically begins with upper abdominal pain that may extend to the back and other areas, and may worsen with food intake. Other symptoms include swollen and tender abdomen, nausea, vomiting, fever, and/or rapid pulse. Acute pancreatitis can have severe complications and high mortality. Currently, there is no specific treatment for the disease. Mild cases can be treated with conservative measures, such as abstinence from any oral intake and intravenous fluid rehydration, while severe cases may require admission to the ICU or even surgery to address complications of the disease. Severe acute pancreatitis (SAP) can result in organ (e.g., heart, lung, and/or kidney) failure, systemic inflammatory response syndrome, shock, bleeding from adjacent vessels or into the pancreas, clotting of adjacent vessels, pancreatic necrosis that can become infected, development of pseudocysts (accumulations of fluid and tissue debris), and/or death. About 20% of acute pancreatitis cases are severe, with a mortality rate of about 20%.

Pancreatic cancer is a malignant tumor of the pancreas. Nearly 40,000 individuals in the United States are diagnosed with this condition and almost an equal number die from the disease each year. Depending on the extent of the tumor at the time of diagnosis, the prognosis is generally regarded as poor, with less than five percent survival at five years after diagnosis. Complete remission is very rare. Most pancreatic tumors are adenocarcinomas. Other types of pancreatic tumors include other tumors of the exocrine pancreas (e.g., acinar cell cancers), intrapancreatic mucinous tumors, mucinous cystadenoma/adenocardinomas, and pancreatic neuroendocrine tumors such as insulinomas and metastatic tumors to the pancreas, such as renal cell carcinomas. Because the symptoms of pancreatic cancer are so non-specific and varied (e.g., including pain in the upper abdomen, loss of appetite, significant weight loss, and jaundice), and typically do not present until the tumor is advanced, early diagnosis is difficult. Thus, pancreatic cancer often is not diagnosed until it is at a stage when it can not be treated.

SUMMARY

The present document is based in part on the development of materials and methods for providing gastroduodenal hypothermia that can be localized to the region of the pancreas and can be placed in a patient using minimally invasive methods. For example, this document discloses the use of devices that can be endoscopically placed in the stomach, adjacent to the pancreas, and can be cooled to induce hypothermia for treatment of diseases such as pancreatitis (including SAP) and pancreatic cancer, while maintaining adequate enteral nutrition of the patient. These materials and methods can halt or slow the inflammatory, cell death, and auto-digestive pathways that result in SAP, as well as cancer growth and spread, resulting in therapeutic benefits to the patient. In addition, the devices described herein provide a simple, low-cost, low-risk, easily implemented treatment that can be used emergently in any medical care setting.

In one aspect, this document features a method for treating a clinical condition in a patient in need thereof, comprising subjecting an organ or a tissue affected by the clinical condition to localized hypothermia. The clinical condition can be severe acute pancreatitis or pancreatic cancer. The method can comprise inserting into the patient a device comprising one or more cooling balloons, and filling all or a portion of at least one of the one or more cooling balloons with a fluid (a gas or a liquid) having a temperature from about 4° C. to about 35° C. (e.g., about 30° C., about 35° C., or about 30-35° C.). The method can comprise inserting a cooling balloon into the stomach of the patient, inserting a cooling balloon into the duodenum of the patient, or inserting cooling balloons into the stomach and duodenum of the patient. The device can be inserted into the patient via the mouth of the patient. The device can be percutaneously inserted into the patient. The device can comprise a hollow tube adapted to extend into the jejunum of the patient, and the method can further comprise providing nutrients directly into the jejunum of the patient via the hollow tube. The device can comprise one or more retention balloons adapted for retaining the one or more cooling balloons at desired locations, and the method can further comprise filling the one or more retention balloons with a fluid (e.g., a radio-opaque fluid). The device can further comprise a radio-opaque marker. The method can further comprise monitoring the location of the device using x-ray.

In another aspect, this document features a device comprising a hollow balloon catheter having a plurality of balloons thereon, wherein at least one of the plurality of balloons is configured for placement in the stomach of a patient, wherein two the plurality of balloons are configured for placement in the duodenum of the patient such that there is a space for the ampulla of Vater, and wherein the device further comprises a distal portion configured for placement in the jejunum of the patient, the distal portion defining one or more ports such that the interior of the device is in fluid communication with the interior of the jejunum. The balloon catheter can have a proximal end with a nasal placement member that permits the balloon catheter to pass through a nostril of the patient. The device can further comprise a radio-opaque marker. The radio-opaque marker can be located distal to the at least one balloon configured for placement in the stomach and proximal to the balloons configured for placement in the duodenum. The radio-opaque marker can be located on a portion of the balloon configured for placement in the stomach, wherein the portion is adapted to be positioned toward the posterior portion of the stomach. The device can have two balloons configured for placement in the stomach of the patient. At least one balloon configured for placement in the stomach can have two or more chambers. At least one of the chambers can be adapted to be positioned toward the posterior portion of the stomach, and another of the chambers can be adapted to be positioned toward the anterior portion of the stomach. Each of the two or more chambers can have an interior in fluid communication with the lumen of one or more hollow connectors.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

This document relates to materials and methods for producing localized hypothermia for treatment of diseases such as pancreatitis (e.g., SAP) and pancreatic cancer. Described herein are materials and minimally invasive methods for providing localized hypothermia (e.g., gastroduodenal hypothermia) near the pancreas while maintaining enteral nutrition. For example, this document discloses treatment of pancreatitis and pancreatic cancer using balloons that can be endoscopically placed in the stomach and/or duodenum, adjacent to the pancreas. Filling these balloons with a relatively cold fluid (i.e., a fluid that is at a lower temperature than the body temperature) can result in hypothermia localized to the region of the pancreas, which can halt or slow the inflammatory, cell death, and auto-digestive pathways that result in SAP, as well as tumor growth and spread associated with cancer.

Non-compliant, stiff balloons distended from about 300 ml to about 700 ml have been left in the stomach from 3 to 12 months for treatment of obesity, with few complications (Genco et al. (2006) *Int J Obes (Lond)* 30:129-133; and Gaggiotti et al. (2007) *Obes Surg* 17:949-956). In addition, capillary perfusion pressure (CPP) averages 25 mm Hg, while interstitial pressure averages 4-6 mm Hg. The minimal distension pressure of the stomach in humans is about 6-8 mm Hg (Mundt and Samsom (2006) *Gut* 55:1725-1730), and 4 mm of Hg can be sufficient to ensure contact between a balloon and stomach wall (Lunding et al. (2006) *Scand J Gastroenterol* 41:544-552). Volumes from 100-700 ml have been used in gastric accommodation studies with periods of sustained distension for up to 10 minutes (Lunding et al., supra). Given the above, using gastric and/or duodenal balloons to generate an increase in interstitial pressure (e.g., a periodic 1-25 mm Hg increase) should not cause mucosal ischemia in the stomach or duodenum.

Figure 1:
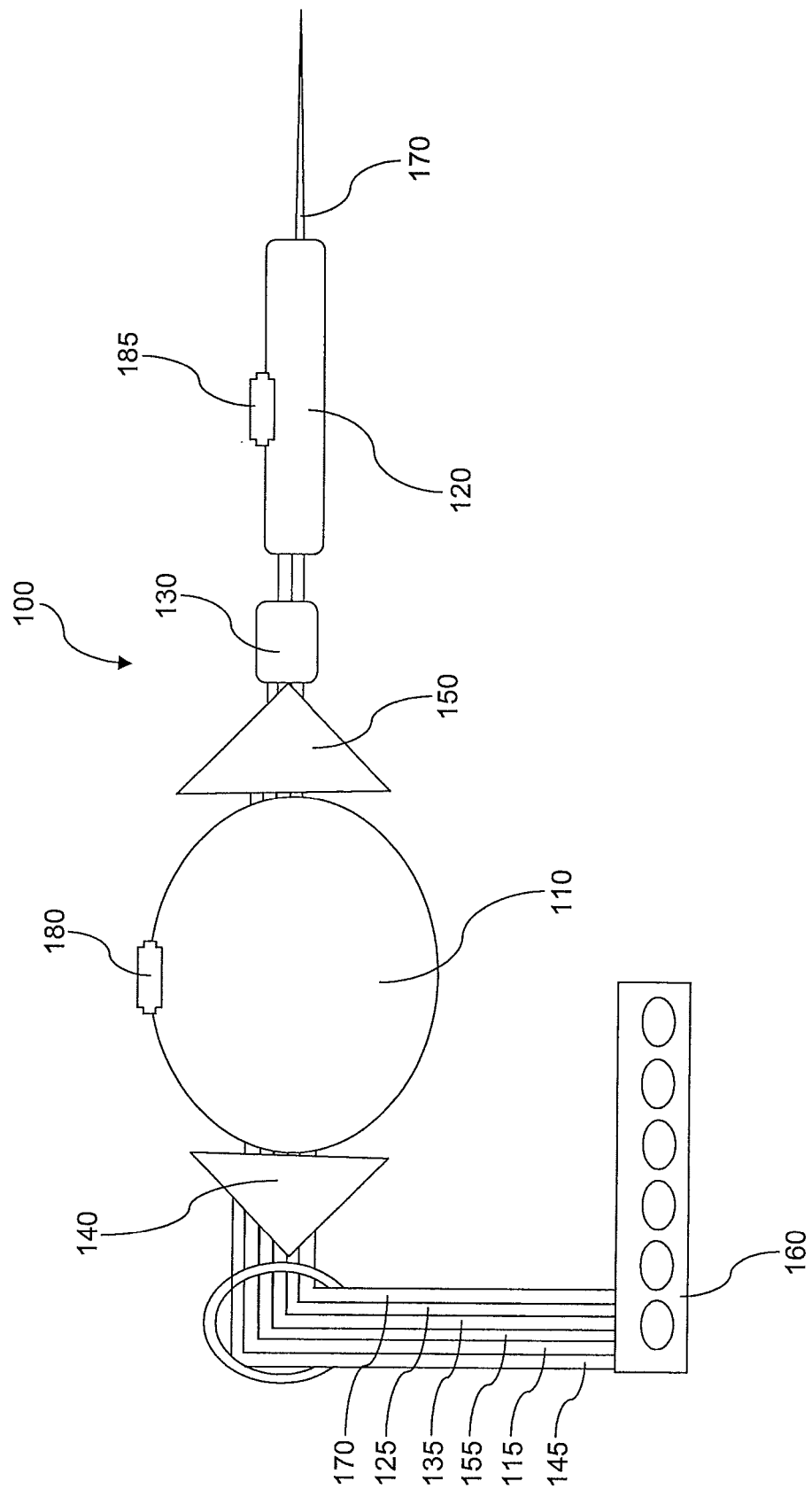
FIG. 1 is a depiction of a device in accordance with some embodiments described herein.
Figure 3:
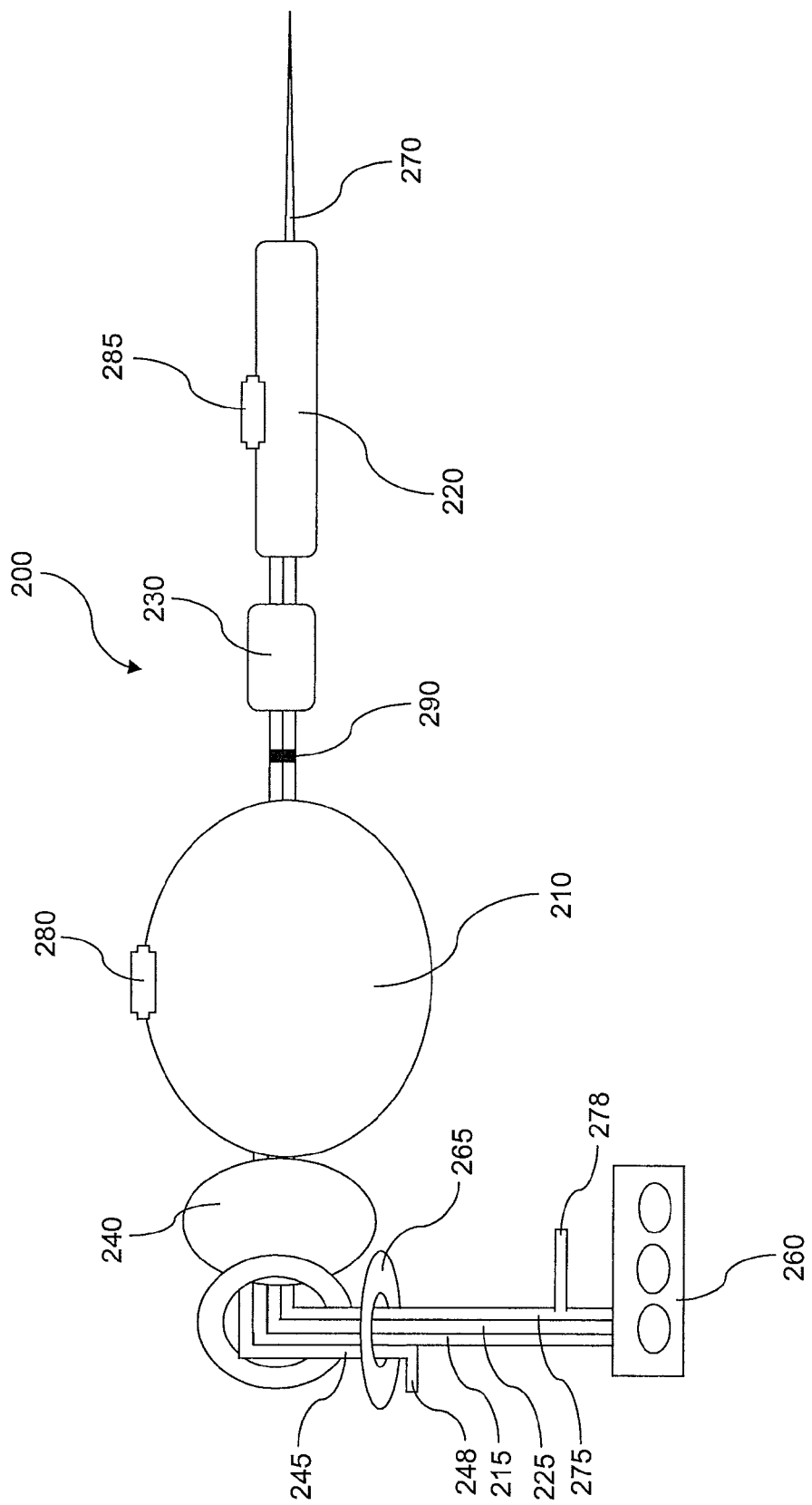
FIG. 3 is a depiction of a device in accordance with some embodiments described herein.
Figure 4:
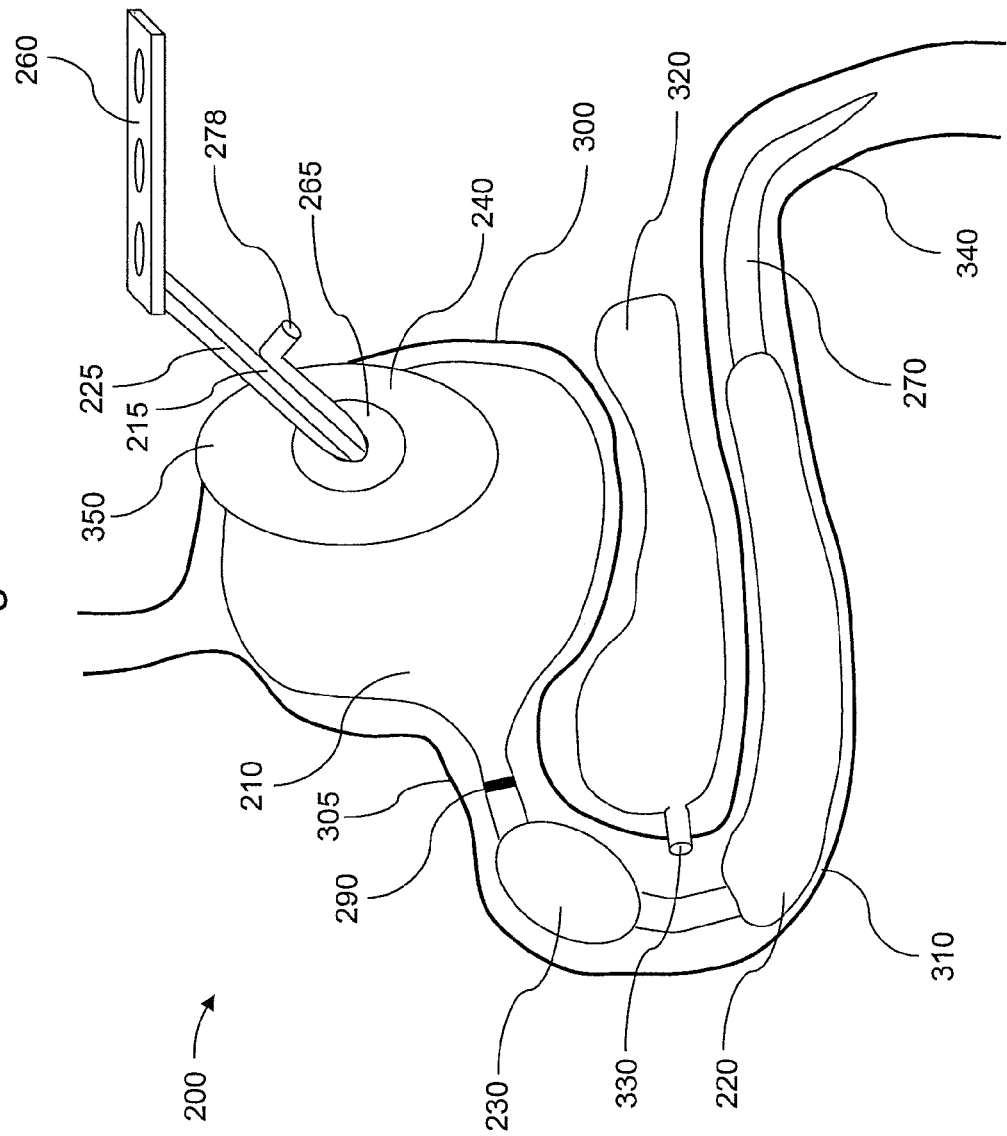
FIG. 4 is a depiction of a device in accordance with some embodiments described herein, placed within the digestive tract.

As described herein, hypothermia can be induced via cold (e.g., 4-35° C.) irrigation through a gastroduodenal balloon tube (see, e.g., FIGS. 1, 3, and 4). Such a device can be endoscopically placed in a patient and can remain in the patient on a short-term or long-term basis. Relatively short-term treatment may be used in the treatment of SAP, for example, such that a device may remain in a patient for several days to several weeks. In some cases, such a device can be placed using an oral endoscope, and then can be converted to a nasal device. A nasal exit can be more comfortable and less intrusive for the patient than an oral exit. In contrast, longer term treatment may be desirable in some cases of SAP or in cases of pancreatic cancer, for example. In such cases, a device as described herein may be placed percutaneously, such that the exit point is via the abdominal wall rather than through the nose or mouth. Patients having such devices may have greater comfort and mobility, for example, and may even be treated on an outpatient basis.

In general, the devices described herein include a balloon catheter having at least a gastric balloon and/or a duodenal balloon. In some embodiments, a device can include more than one duodenal balloon, and/or one or more means for retaining the device in the proper position within a patient. For example, a device can have a balloon for pyloric retention and/or a balloon for esophageal retention, which, when inflated, can serve to prevent a gastric balloon from migrating beyond the pylorus or the esophageal sphincter, respectively. In some cases (e.g., for percutaneous placement), a device can include a second gastric "bumper" balloon that can be adapted for positioning next to the stomach wall at the opening through which the device was inserted. Inflation of this balloon can prevent the gastric balloon from being pulled out of the stomach.

The devices provided herein also can include a jejunal tube that extends past the duodenal balloon and beyond the ligament of Treitz. The jejunal tube can be used for feeding, such that nutrients can be passed directly into the jejunum, bypassing the pancreas. In some embodiments, a jejunal tube can have a one or more feeding ports through which nutrients can be passed. For example, a jejunal tube can have one or more feeding ports along its sides and/or at its distal end. In addition or alternatively, a jejunal tube can have a weighted distal end and/or a distal loop that can facilitate endoscopic placement. See, e.g., FIGS. 6-8. A distal loop also can be used to tether the distal end of a device.

The devices provided herein can have any suitable dimensions. In some embodiments, for example, a device can have a length sufficient to extend from the nostril to the jejunum, plus enough length at the proximal end for connection with one or more control apparatuses (e.g., pumps and temperature or pressure monitors). In embodiments for percutaneous placement, a device can have a length sufficient to extend from the external surface of the abdomen to the jejunum, plus enough length to allow for connection with one or more control devices. A device can have, for example, a length from about one foot to about ten feet (e.g., about one, about two, about three, about four, about five, about six, about seven, about eight, about nine, or about ten feet). Further, a device can have an uninflated diameter suitable for passage through an endoscope. For example, the uninflated diameter of a device can range from about one mm to about 15 mm (e.g., about one, about two, about three, about four, about five, about six, about seven, about eight, about nine, about ten, about 11, about 12, about 13, about 14, or about 15 mm). In some embodiments, all or a portion of the device can be contained within an elongate, flexible outer sheath. In use, the device and the sheath can be positioned in a patient, the outer sheath can be removed, and the balloon(s) can be inflated.

A tube (e.g., a balloon tube and/or a jejunal tube) can be made of a flexible material including, without limitation, plastic, silicone, or rubber, and can be calibrated along its length (e.g., starting from the jejunal end). A balloon can be made of an elastic or non-elastic material, including, without limitation, plastic, polyethylene, nitrile, cellophane, rubber, silicone, or other materials that can conform to the contours of the surrounding structures. Each balloon can be connected to one or more single lumen or double lumen tubes that can have at least one open end, can have an elongate configuration, and can be in fluid communication with the interior of the balloon. If the interior of a balloon is in fluid communication with the lumen of a double lumen tube or two single lumen tubes, for example, one lumen or one tube can be used to pass fluid into the balloon while the other lumen/tube can be used to remove fluid from the balloon. This can be done simultaneously or on an alternating basis, and can provide continuous perfusion, which can maintain a constant temperature of the fluid in the balloon. Continuous perfusion can be conducted at a constant pressure or by actively perfusing and suctioning out a constant volume at the same time. In addition, a balloon can have a port (e.g., a tube) adapted for monitoring pressure within the balloon. A pressure monitoring port can be the same as or separate from a tube used for passing fluid into/out of the balloon.

Figure 6:
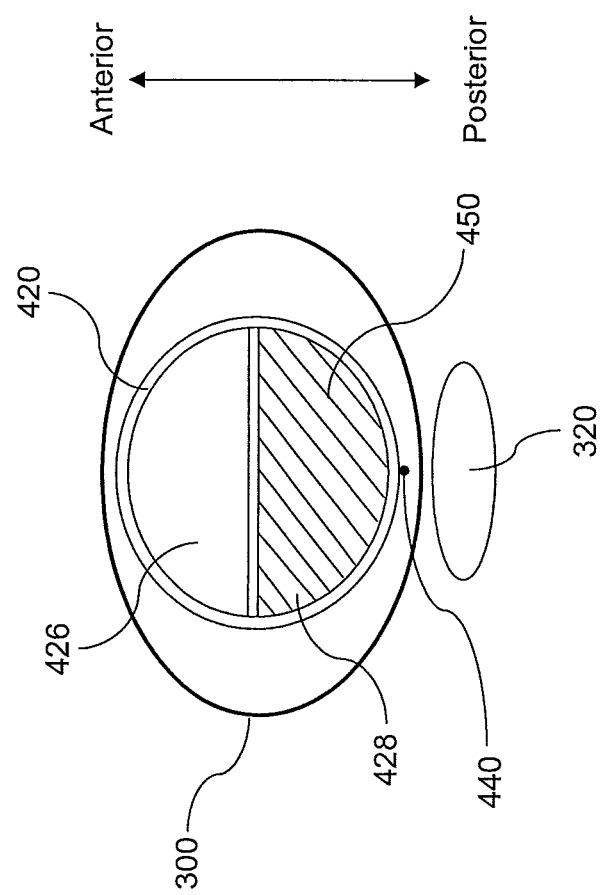
FIG. 6 is a depiction of a gastric balloon in accordance with some embodiments described herein, placed in the stomach.
Figure 7:
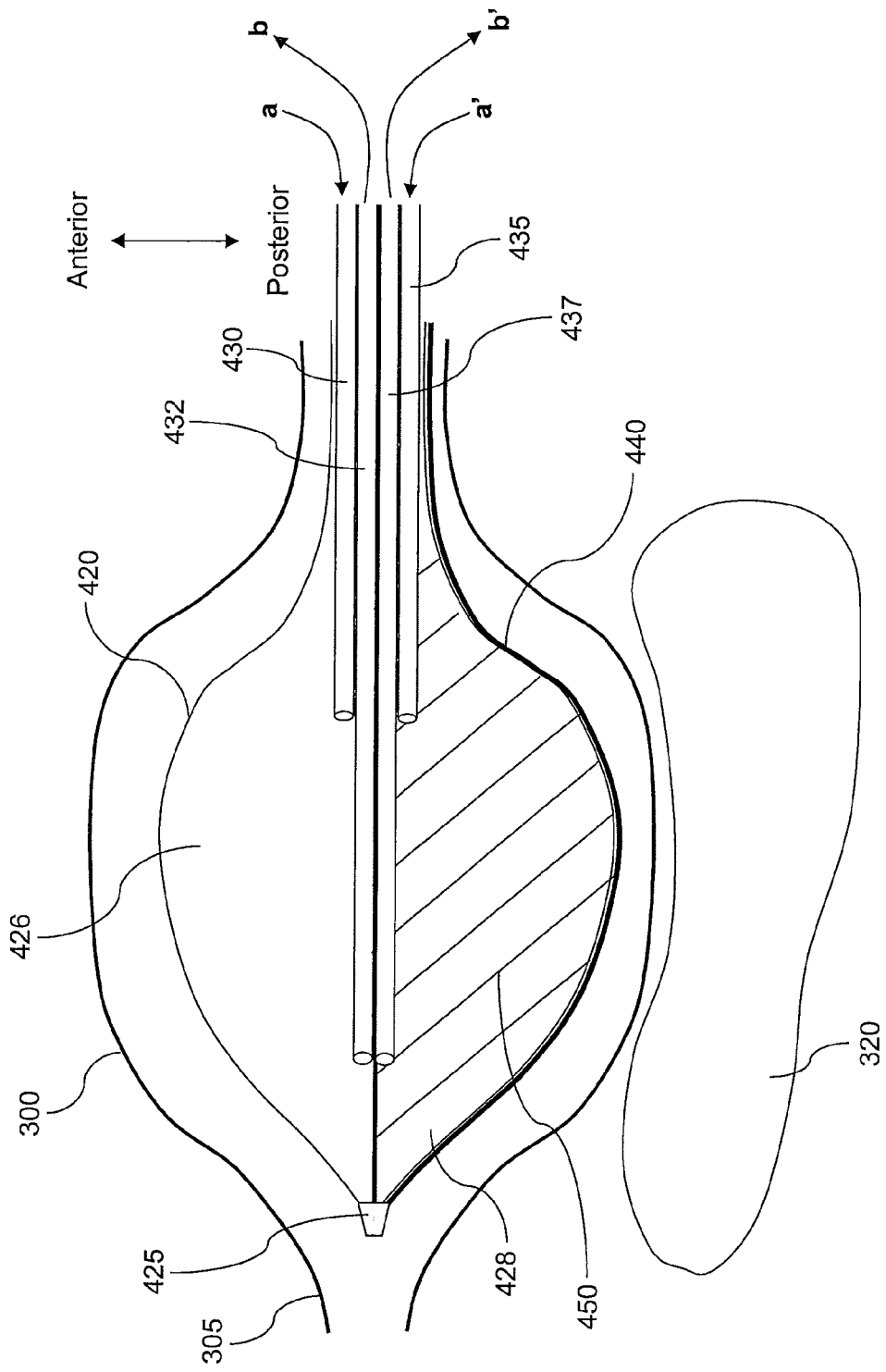
FIG. 7 is a depiction of a device in accordance with some embodiments described herein, placed in the stomach.
Figure 8:
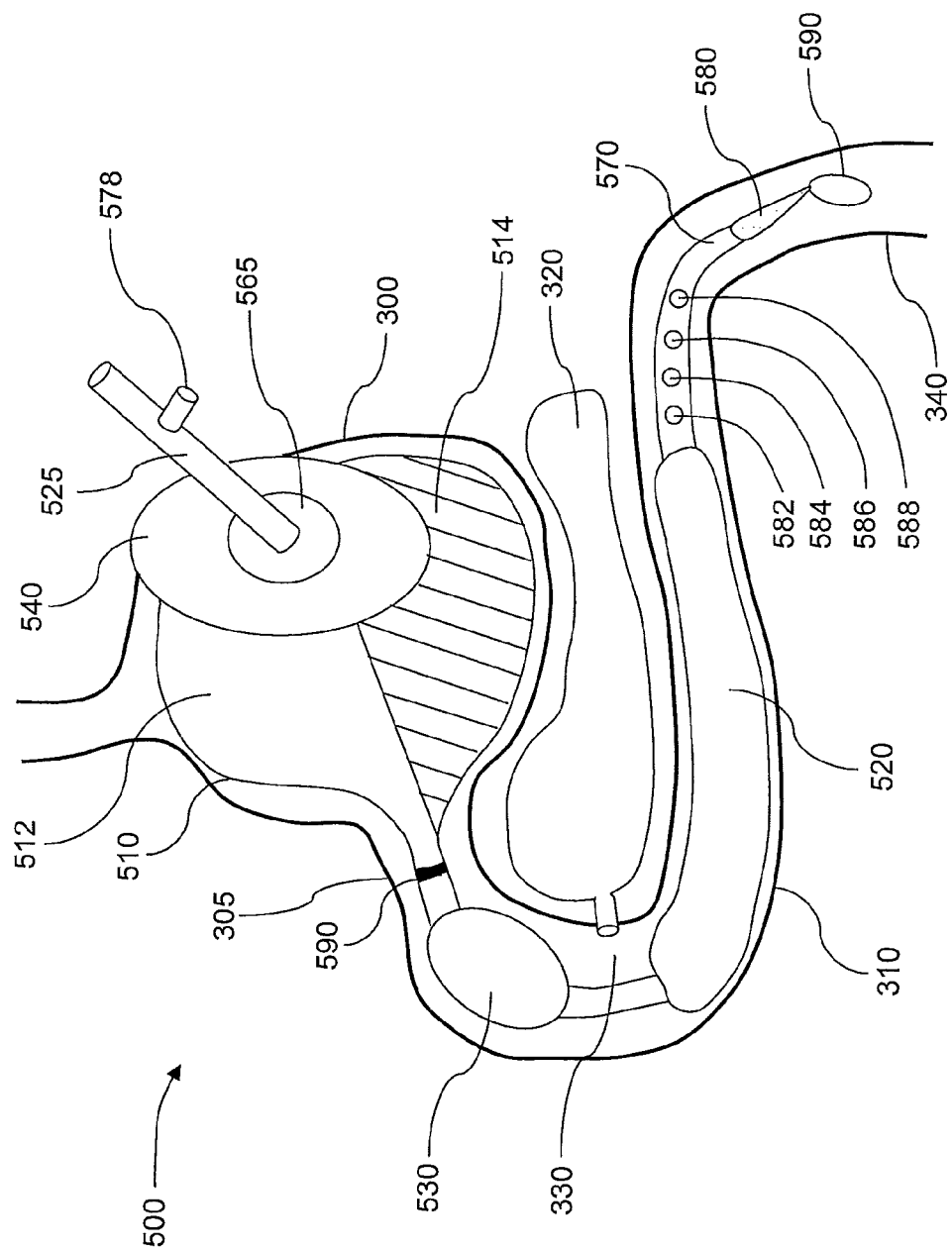
FIG. 8 is a depiction of a device in accordance with some embodiments described herein, placed in the digestive tract.

In some embodiments, a balloon (e.g., a gastric balloon) can have two or more chambers (see, e.g., FIGS. 6-8). In an embodiment having two chambers, for example, the chamber that is placed adjacent to the pancreas (i.e., the posteriorly positioned chamber) can be filled with a relatively cold fluid, while the other chamber can be filled with a fluid that is at or about body temperature. The chamber that is not adjacent to the pancreas can maintain the posterior chamber in position adjacent to the pancreas. Such balloons can be used to provide more specifically localized hypothermia in the area of the pancreas, while maintaining other portions of the stomach at or near normal body temperature. In addition, the anterior chamber can be filled with a gas (e.g., air), which can maintain the dorsal chamber in position while being lighter than a liquid-filled chamber. Having two or more chambers can provide for flexibility during treatment. For example, the anterior chamber can be periodically deflated, while the posterior chamber can be maintained in an inflated configuration. In embodiments where a balloon has two or more chambers, each chamber can have one or more hollow, elongate tubes with a lumen in fluid communication with the interior of the chamber. Fluid can be passed into and/or out of the chambers through the tube(s). In addition, in some cases the tube(s) can be used to monitor pressure within the balloon.

In some embodiments, one or more of the balloons (e.g., the gastric and duodenal balloons) can have a pressure transducer. The balloons can be inflated automatically with a liquid or gas fluid, and can inflate simultaneously or individually. In some cases, inflation of gastric and duodenal balloons can occur in an alternating fashion (e.g., at 1 to 5 minute intervals). Each balloon can remain inflated for about 1 to 20 minutes (e.g., about 1, 2, 3, 4, 5, 6, 7, 8, 9, 10, 11, 12, 13, 14, 15, 16, 17, 18, 19, or 20 minutes). Typically, the balloon(s) can be adapted for inflation to about two to about 100 cm water (e.g., about 2, about 3, about 5, about 7, about 10, about 15, about 20, about 50, or about 100 cm water). A gastric balloon can have a volume from about 100 cc to about 3000 cc (e.g., about 100, about 150, about 200, about 250, about 300, about 400, about 500, about 600, about 700, about 750, about 800, about 900, about 1000, about 1500, about 2000, about 2500, or about 3000 cc). A duodenal balloon can have a volume of about 5 to about 300 cc (e.g., about 5, about 10, about 20, about 25, about 30, about 50, about 75, about 100, about 150, about 200, about 250, or about 300 cc). A retention balloon can have a volume of about 1 to about 200 cc (e.g., about 1, about 2, about 3, about 4, about 5, about 6, about 7, about 8, about 9, about 10, about 15, about 20, about 25, about 30, about 50, about 75, about 100, about 125, about 150, or about 200 cc).

The balloons can have any suitable shapes. In some cases, a balloon can be configured to have a spherical, ovoid, conical, pyramidal, apple-like, or tube-like shape when inflated in the absence of surrounding structures. As noted above, however, the balloons may conform to the shape of surrounding structures when inflated in the body of a patient.

In some cases, a balloon (e.g., a gastric balloon) can have a weighted distal end, which can facilitate placement within the stomach. In some embodiments, a retention balloon (e.g., a balloon configured for pre-pyloric or post-esophageal placement) can have a conical shape when inflated, with the tip of the cone adapted to extend into or against the pylorus or the esophagus, respectively. In some cases, a retention balloon can have a spherical, discoid, or other shape, with a diameter that is greater than the diameter of the pyloric or esophageal opening, or the opening from the stomach through the abdominal wall in the case of percutaneously placed devices. For example, a retention balloon can have a diameter at its widest point of about two cm to about ten cm (e.g., about two, about three, about four, about five, about six, about seven, about eight, about nine, or about ten cm).

A device as provided herein can be inserted into a patient via the mouth or nose, using standard endoscopic methods with or without a guidewire or fluoroscopic guidance. In some embodiments, after placement of balloons in the stomach and/or duodenum via the mouth, the device can be converted to extend through the nose of the patient by addition of a nasal piece. For example, a clinician can pass a nasal piece through the nose and into the mouth, connect the nasal piece with the portion of the device coming out though the mouth, and pull on the nasal end to bring the oral end through the nose. Nasal placement can be particularly useful for relatively short-term treatment (e.g., for treatment of SAP), although nasal placement also can be used for long-term treatment (e.g., for treatment of pancreatic cancer). Once the device is in place, it can be connected to an infusion pump capable of filling and deflating the balloons. The retention balloon(s), if present, can be inflated such that the gastric and duodenal balloons will be maintained in their desired locations. The device also can be connected to one or more controllers by which the temperature of the liquid and pressure in the balloons can be monitored and regulated.

In some embodiments, a device as provided herein can be percutaneously inserted into a patient. Methods for percutaneous placement include, without limitation, percutaneous endoscopic gastroscopy (PEG), which is an endoscopic procedure for placing a tube into the stomach through the abdominal wall. Techniques for placing PEG tubes are known in the art, and can include performing a gastroscopy to evaluate the anatomy of the stomach, identifying the anterior stomach wall, ensuring that no organs are present between the wall and the skin, and puncturing the abdominal wall through a small incision using an angiocath. In some cases, a wire can be placed into the stomach, and a series of dilators can be used to increase the size of the passage through the skin and abdominal wall. An endoscope can be passed through the channel into the stomach after the channel has matured (e.g., over the course of several weeks), and a device as provided herein can be placed in the patient via the endoscope with or without a guidewire or fluoroscopic guidance. In some embodiments, a device can initially be placed in a patient via the mouth/nose, and then can be replaced by a device that is placed percutaneously (e.g. for long-term treatment). This can be useful, for example, to begin hypothermia treatment quickly, while allowing for eventual treatment that gives the patient relatively more comfort and freedom of mobility, for example.

The internal localization of the devices provided herein can be closely monitored. While the position of a device as provided herein may be directly visualized (e.g., via an endoscope) during placement, in some embodiments the devices provided herein can include a means for monitoring the position of the device during and after placement in a patient. In some cases, a device can include a radio-opaque marker such as, for example, tungsten, stainless steel, high molecular weight polyethylene, TEFLON®, titanium, or aluminum, to allow a clinician to visualize the position of the device using, e.g., x-ray. For example, a device can have a radio-opaque marker on its surface between the gastric balloon and the duodenal balloon (or, in some cases, the most proximal duodenal balloon) at the portion of the device that is to be placed at the pylorus. Examples of such embodiments are depicted in FIGS. 3 and 4, for example. In some cases, a balloon of a device (e.g., a pre-pyloric retention balloon or a separate marker balloon) can be filled with a radio-opaque solution such as, for example, HYPAQUE™ (diatrizoate Sodium; sodium 3,5-diacetamido-2,4,6-triiodobenzoate), which also can permit a clinician to monitor the position of the device via x-ray. In some cases, a device as described herein can have a radio-opaque marker extending in a line or other pattern along all or a portion of its exterior (e.g., in a line parallel to the longitudinal axis of the device). For example, a device can have a radio-opaque marker on its external surface parallel to its longitudinal axis, particularly on the portion of the external surface that is to be positioned most posteriorly. See, for example, FIGS. 5-7. Visualization by other means (e.g., ultrasound) also may be useful.

The external portion of the device can be firmly but releasably anchored to the nose or the external abdominal surface, for example. During placement and for long term treatment, the patient can remain supine so as to keep the cold liquid dependent and over the pancreas to facilitate pancreatic cooling. The devices provided herein also can be combined with a local cooling device placed on the skin or implanted subcutaneously in the posterior abdominal wall in the area overlying the pancreas (i.e., even with vertebrae L1-L3 on the left side).

After the device is inserted into a patient, the gastric balloon can be inflated (e.g., to a pressure that is less than or equal to normal gastric pressure after a meal) with a cold fluid (e.g., water, saline, or a gas). Inflation can be to about 2 to about 10 cm water, although in some cases it may be useful to inflate a gastric balloon up to 100 cm water). The duodenal balloon(s) also can be inflated. For example, the gastric and duodenal balloons can be inflated or irrigated with a solution at a temperature that will cause the internal temperature of the balloons to be about 4° C. to about 35° C. (e.g., about 5° C., about 10° C., about 15° C., about 20° C., about 25° C., about 30° C., about 31° C., about 32° C., about 33° C., about 34° C., about 35° C., about 5-10° C., about 10-15° C., about 15-20° C., about 20-25° C., about 25-30° C., about 30-33° C., about 31-34° C., about 32-35° C., about 30-34° C., about 31-35° C., or about 30-35° C.). In some cases, inflation of a gastric balloon can periodically alternate with cold irrigation of one or more duodenal balloons (avoiding the ampullary area). Temperature regulation of a balloon infusate can be achieved with, for example, the aid of a thermocoupler placed in the wall of the balloon, which can be activated when the balloon is deflated. In some embodiments, a gastric balloon can be kept in place with a pre-pyloric or esophageal balloon (or both) that are maintained in a continuously inflated state with, e.g., HYPAQUE™. Any of the balloons can be designed to automatically deflate and activate an alarm if the pressure exceeds a certain level (e.g., 50 mm Hg for 3 minutes or more, which can signal distal migration), preventing distal migration of the tube. Pressure, temperature, volume, and placement of the balloons typically are closely monitored during use.

The devices provided herein can have significant advantages over other known devices (e.g., those set forth in U.S. Pat. No. 6,726,708, and U.S. Patent Appl. Pub. No. 2004/0210281). These include, for example, reduced discomfort to the patient since there is only a single nasal tube and a single endoscopic placement, or a percutaneous placement with no nasal tube for long-term treatment; the option to feed jejunally while the tube is in situ (recommended in acute pancreatitis in order to maintain the gut mucosal barrier); lower risk of aspiration; and lower risk of pressure necrosis, allowing for prolonged placement as is often necessary with severe acute pancreatitis. Table 1 provides a comparison of the presently disclosed devices with previous devices.

TABLE 1

Comparison of present and previously known devices

| Feature | Previous devices | Present device |
|---|---|---|
| Number of balloons/system | 1 | 3-4 |
| Jejunal feeding tube extension | Absent or unclear (not mentioned) | Present |
| Possible placement duration | Hours to a few days | Days to months |
| Route | Oral | Nasal or percutaneous |
| Simultaneous duodenal and stomach balloon placement | Separate endoscopic intubations | Single endoscopic intubation |
| Numbers of tubes needed for stomach and duodenum, exit site | 2 (both from mouth) | 1 (nasal or percutaneous) |
| Inconvenience and discomfort to patient | High | Low |
| Alternate inflation timing, volume, pressure, balloon alarms | Absent | Present |
| Pyloric retainer | Absent | Present |
| Risk of displacement or pressure necrosis | High | Low |
| Temperature regulation | Outflow fluid temperature | Thermocouple (mucosal temp.) |
| Space to accommodate ampulla of Vater | Absent | Present |
| Mechanism of retaining location | Distance from incisors, local pressure | Retaining balloons |
| Ability to confirm location by x-ray | Imprecise | Precise |
| Temperature, flow rate of fluid | Targets weight loss (lower temp, high flow - measured as Kcal/min) | Targets cell death, inflammation, and proliferation (higher temp) |
| Cooling balloons | Gastric | Gastric (emergent), gastro-duodenal (long term) |
| Stomach cooling | All over | Posterior/postero-inferior wall |
| Nature of fluid | May be heavy (e.g., water) to provide satiety | May be light (e.g., gas) to allow retention in stomach |
| Placement | Usually via PEG | Via naso-gastro (emergent) and PEG (long term) |
| Nutrition port | Optional | Present in gastro-duodenal tube |
| Warming blankets | Only if necessary | Routinely used |

Turning now to the figures, FIG. 1 depicts an embodiment of a device as provided herein. Device 100 can have gastric balloon 110 and first duodenal balloon 120. Gastric balloon 110 can be configured for placement in the stomach, while first duodenal balloon 120 can be configured for placement in the duodenum. In some embodiments (e.g., as depicted in FIG. 1), device 100 also can have second duodenal balloon 130, which also can be configured for placement in the duodenum (e.g., proximal to first duodenal balloon 120 and distal to gastric balloon 110). In some cases, device 100 also can include proximal retention balloon 140 and/or distal retention balloon 150. Proximal retention balloon 140 can be adapted for fundic placement, for example, while distal retention balloon 150 can be adapted for pyloric placement.

Device 100 also can include controller means 160, which can be linked to external devices such as, without limitation, one or more infusion pumps, pressure monitors, and/or temperature monitors. Controller means 160 also can be linked to the balloon members of device 100 via connectors 115, 125, 135, 145, and 155, which can be, for example, tubes with hollow lumens in fluid connection with gastric balloon 110, first duodenal balloon 120, second duodenal balloon 130, proximal retention balloon 140, and distal retention balloon 150, respectively. Connectors 115, 125, 135, 145, and 155 can be configured to extend between controller means 160 and balloons 110, 120, 130, 140, and 160 via the mouth or nose and esophagus of a patient, or via a percutaneous passage. In use, fluid can be passed through the connectors and into or out of the balloons.

In some embodiments, device 100 also can include jejunal extension tube 170. The proximal end of jejunal extension tube 170 can be connected to controller means 160, or can be separate from controller means 160. The distal end of jejunal extension tube 170 can extend beyond the distal portion of first duodenal balloon 120, and can be adapted for placement in the jejunum of a patient. Further, the distal portion of jejunal extension tube 170 can define one or more ports through which nutrients can be passed into the patient.

A pump connected to controller means 160 can be used to move nutrients through jejunal extension tube 170 and into the patient.

In some cases, a device as provided herein can have thermocouple sensors positioned on the gastric and/or duodenal balloon(s). As depicted in FIG. 1, for example, device 100 can have thermocouple sensors 180 and 185 positioned on gastric balloon 110 and first duodenal balloon 120, respectively. Thermocouple sensors 180 and 185 can be connected to controller means 160, and can be used to regulate the rate of temperature change and to regulate the temperature of the infusate(s) placed in to the balloons, for example.

Figure 2:
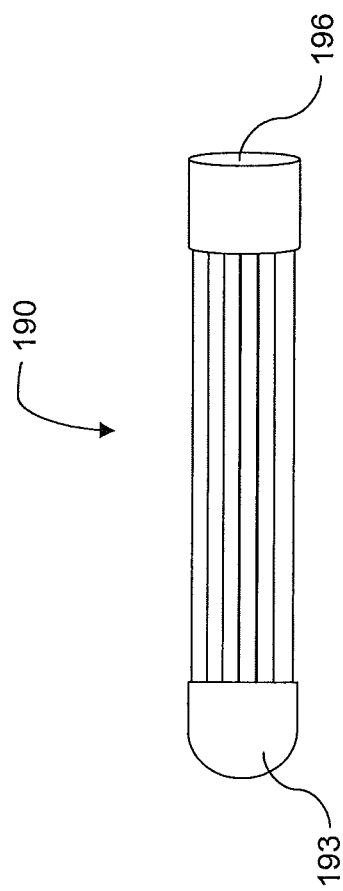
FIG. 2 is a depiction of a nasal piece of a device in accordance with some embodiments described herein.

Device 100 also can have nasal member 190 (FIG. 2), which can be reversibly attached to device 100. Nasal member 190 can be adapted for placement through the nostril of a patient, and can connect controlling means 160 with connectors 115, 125, 135, 145, and 155, as well as with jejunal extension tube 170. Nasal member 190 can have one or more removable caps (e.g., removable cap 193) on one or both of its ends to, for example, facilitate passage of nasal member 190 through the nostril of a patient. In some embodiments, nasal member 190 also can have adapter 196, which can be removably positioned on a portion nasal member 190, such as at the portion of nasal member 190 that will be connected with the rest of device 100 when device 100 is in use in a patient.

FIG. 3 depicts another embodiment of a device as provided herein (e.g., devices for percutaneous placement). Device 200 can have gastric balloon 210 and first duodenal balloon 220. Gastric balloon 210 can be configured for placement in the stomach, while first duodenal balloon 220 can be configured for placement in the duodenum. In some embodiments (e.g., as depicted in FIG. 3), device 200 also can have second duodenal balloon 230, which also can be configured for placement in the duodenum (e.g., proximal to first duodenal balloon 220 and distal to gastric balloon 210). In some cases, device 200 also can include proximal bumper balloon 240. Proximal bumper balloon 240 can be adapted for placement in the stomach adjacent to the stomach wall, for example, and can prevent gastric balloon 210 from being pulled out of the stomach/body via the percutaneous opening. In some cases, device 200 can be percutaneously inserted into a patient, balloon 240 can be inflated, and a clinician can pull on device 200 until balloon 240 is against the stomach wall, which can indicate correct placement of device 200 in the patient.

Device 200 also can include controller means 260, which can be linked to external devices such as, without limitation, one or more infusion pumps, pressure monitors, and/or temperature monitors. Controller means 260 also can be linked to the components of device 200 via connectors 215, 225, and 245, which can have, for example, hollow lumens in fluid connection with gastric balloon 210, first and/or second duodenal balloons 225 and 235, and proximal bumper balloon 245, respectively. Connectors 215, 225, and 245 can be configured to extend between controller means 260 and balloons 210, 220, and 240 via the mouth or nose of a patient, or via the body surface of a patient. In use, fluid can be passed through the connectors and into and/or out of the balloons.

In some embodiments, device 200 also can include jejunal extension tube 270. The proximal end of jejunal extension tube 270 can be connected to controller means 260, or can be separate from controller means 260 (e.g., via port 278 on connector 275). For example, a pump connected to controller means 260 or to the proximal end of jejunal extension tube 270 can be used to move nutrients through jejunal extension tube 270 and into the patient. The distal end of jejunal extension tube 270 can extend beyond the distal portion of first duodenal balloon 220, and can be adapted for placement in the jejunum of a patient. Further, the distal portion of jejunal extension tube 270 can define one or more ports through which nutrients can be passed into the patient.

In embodiments in which the device is to extend through the body surface of the patient, device 200 can have skin guard 265, which can be reversibly attached to the external surface of the patient. Skin guard 265 can, for example, serve as a marker of the length of the device from the bumper balloon or the length of the device inside a patient. In addition, skin guard 265 can help to retain the device in a fixed position, by virtue of its friction with the device. Skin guard 265 also may serve to attach device 200 to the skin of a patient, protect the body surface from chafing by the external tubing of device 200, and/or help to maintain sterility of device 200.

Connectors 215, 225, and 245 also can have one or more external ports that are not connected to controller 260. For example, connector 245 can have port 248, through which proximal bumper balloon can be inflated or deflated (e.g., by a pump that is not connected to controller 260).

In some embodiments, device 200 can include thermocouple sensors 280 and 285 positioned on gastric balloon 210 and first duodenal balloon 220, respectively. Thermocouple sensors 280 and 285 can be connected to controller means 260, and can be used to regulate the rate of temperature change and to regulate the temperature of the infusate(s) placed in to the balloons.

Device 200 also can have, in some cases, radio-opaque marker 290. Radio-opaque marker 290 can be used to visualize and facilitate placement of device 200 in a patient. For example, as shown in FIG. 3, radio-opaque marker 290 can be positioned distal to gastric balloon 210, such that marker 290 is located at the pylorus when device 200 is properly positioned in a patient. In some embodiments, radio-opaque marker 290 can be located near the distal end of the tube, such that it is located in the jejunum when device 200 is properly positioned in a patient. The location of the radio-opaque marker can be confirmed using abdominal x-ray and the vertebral body (e.g., lumbar vertebrae) as a reference.

FIG. 4 depicts device 200 in a patient. Gastric balloon 210 can be positioned in stomach 300, and first and second duodenal balloons 220 and 230 can be positioned in duodenum 310 (which curves around pancreas 320), such that radio-opaque marker 290 is positioned at pylorus 305. In some embodiments, first and second duodenal balloons 220 and 230 can be configured and positioned such that there is space for ampulla of Vater 330. As shown, jejunal extension tube 270 can extend into jejunum 340 of the patient. Proximal bumper balloon 240 can be positioned within the interior of stomach 300 adjacent to the percutaneous opening, to prevent gastric balloon 210 from being pulled out of stomach 300. Skin guard 265 can be attached to external surface 350 of the patient. The connectors (e.g., connectors 215 and 225) can extend through the abdominal wall of the patient and can be connected to controller means 260. By passing cold fluid through the connectors and into gastric balloon 210 and duodenal balloons 220 and 230, either simultaneously or separately (e.g., in an alternating fashion), localized hypothermia can be produced in the areas surrounding pancreas 320, providing treatment for, e.g., pancreatic cancer and pancreatitis.

Figure 5:
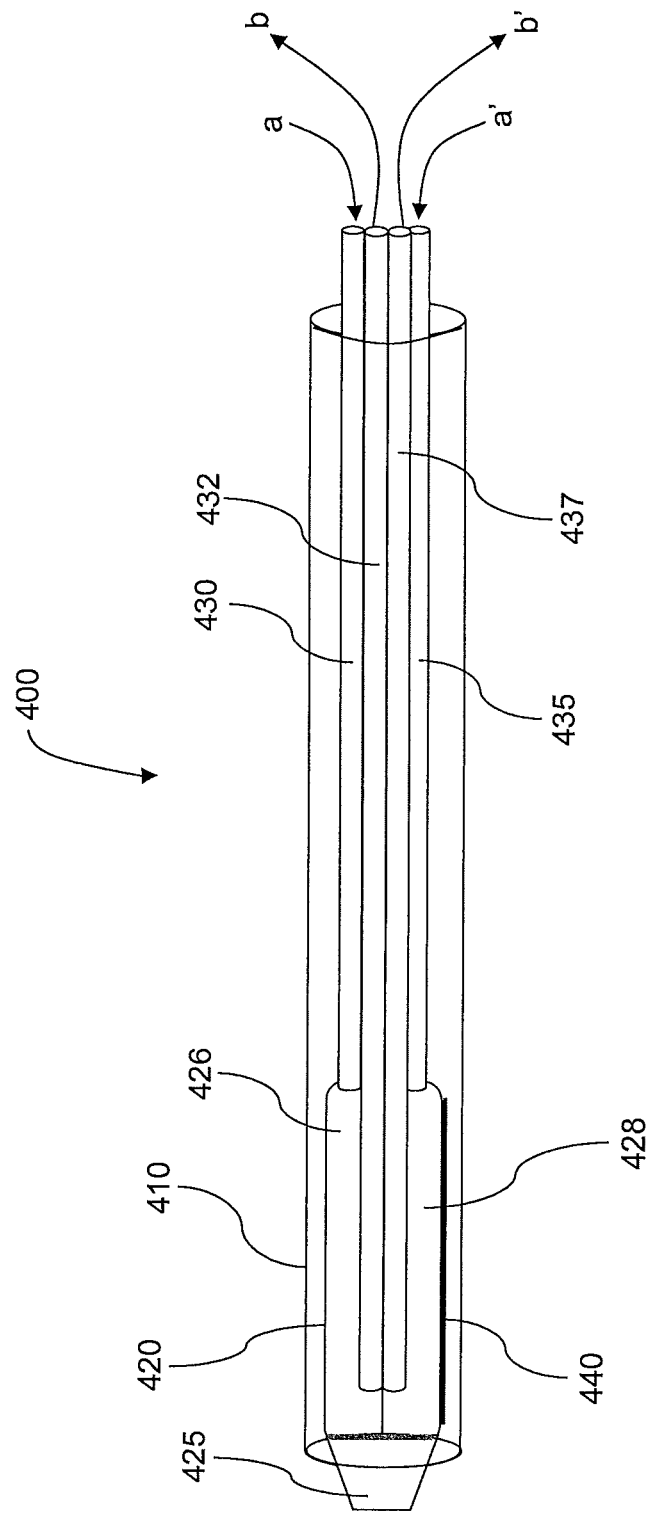
FIG. 5 is a depiction of a device in accordance with some embodiments described herein.

FIG. 5 depicts another embodiment of a device as provided herein. Device 400 can have outer sheath 410 which, prior to placement and deployment of device 400 in a patient, can contain gastric balloon 420 and connectors such as hollow elongate tubes 430, 432, 435, and 437. In some embodiments, gastric balloon 420 can have weighted distal tip 425. Gastric balloon 420 can be divided into two or more chambers (e.g., as shown in FIG. 5, first chamber 426 and second chamber 428). The interior of first chamber 426 can be in fluid communication with the lumens of elongate tubes 430 and 432, while the interior of chamber 428 can be in fluid communication with the lumens of elongate tubes 435 and 437. In some embodiments, as indicated by arrows "a," "b," "a'," and "b'" in FIG. 5, tubes 430 and 435 can be adapted to transfer fluid into chambers 426 and 428, respectively, while tubes 432 and 437 can be adapted to remove fluid from chambers 426 and 428, respectively. An external surface of device 400 (e.g., second chamber 428, as shown in FIG. 5) can have disposed thereon radio-opaque marker 440, which can be used to orient gastric balloon 420 within the stomach of a patient.

FIG. 6 depicts an end view of gastric balloon 420 in stomach 300. Radio-opaque marker 440 can be used to indicate the position of balloon 420 in stomach 300, such that first chamber 426 is positioned anteriorly, while second chamber 428 is positioned posteriorly, adjacent to pancreas 320. Second chamber 428 can be filled with fluid 450, which can be used to specifically cool the area adjacent to pancreas 320. Chamber 426 can be filled with the same or a different type of fluid (e.g., the same type of fluid as fluid 450 but at a higher temperature than fluid 450, or a different type of fluid, such as a fluid that has a lighter weight than fluid 450).

FIG. 7 depicts a side view of device 400 in stomach 300. Again, radio-opaque marker 440 can be positioned along the dorsal portion of stomach 300, such that second chamber 428 is adjacent to pancreas 320. Weighted distal tip 425 can be positioned at or near pylorus 305. A first fluid can be transferred into first chamber 426 of gastric balloon 420 via tube 430 (arrow "a"), and removed from first chamber 426 via tube 432 (arrow "b"). Cooled fluid 450 can be transferred into second chamber 428 via tube 435 (arrow "a'," and removed from second chamber 428 via tube 437 (arrow "b").

FIG. 8 depicts another embodiment of a device as provided herein placed percutaneously in the digestive tract. Device 500 can have gastric balloon 510 and first duodenal balloon 520. Gastric balloon 510 can be configured for placement in stomach 300, while first duodenal balloon 520 can be configured for placement in duodenum 310. As depicted in FIG. 8, device 500 also can have second duodenal balloon 530, which can be configured for placement in the duodenum proximal to first duodenal balloon 520 and distal to gastric balloon 510. First and second duodenal balloons 520 and 530 can be configured and positioned such that there is space for ampulla of Vater 330. Gastric balloon 510 can have first chamber 512 and second chamber 514, and can be positioned such that the chamber to be filled with cold fluid (as depicted, chamber 514) is positioned posteriorly, adjacent to pancreas 320.

Device 500 also can include jejunal extension tube 570, which can extend into jejunum 340. Distal portion 580 of jejunal extension tube 570 can define one or more ports (e.g., ports 582, 584, 586, and 588) through which nutrients can be passed into the patient. In some embodiments, distal portion 580 also can have connected thereto loop 590, which can, for example, facilitate placement of device 500 in a patient.

In some embodiments, device 500 also can have bumper balloon 540, which can be positioned in the interior of stomach 300 adjacent to the percutaneous opening. In addition, device 500 can have skin guard 565, which can be reversibly attached an external surface of the patient into which device 500 is placed. Skin guard 565 can, for example, serve to attach device 500 to the skin of a patient, protect the body surface from chafing by external tubing of device 500, and/or help to maintain sterility of device 500.

Device 500 can have connectors (e.g., connectors 525 and 578), which can be in fluid communication with one or more of balloons 510, 520, and 530, and/or jejunal extension tube 570. Connectors 525 and 578 may or may not be connected to a controller. Device 500 also can have a radio-opaque marker (e.g., radio-opaque marker 590), which can be used to visualize and facilitate placement of device 500 in a patient. As shown in FIG. 8, radio-opaque marker 590 can be positioned distal to gastric balloon 510, such that marker 590 is located at pylorus 305 when device 500 is properly positioned. In some embodiments, a radio-opaque marker can be located along a posterior surface of gastric balloon 510, or near distal portion 580 of jejunal extension tube 570, such that it is located in the jejunum when device 500 is properly positioned in a patient. The location of the radio-opaque marker can be confirmed using abdominal x-ray and the vertebral body (e.g., lumbar vertebrae) as a reference.

Figure 9:
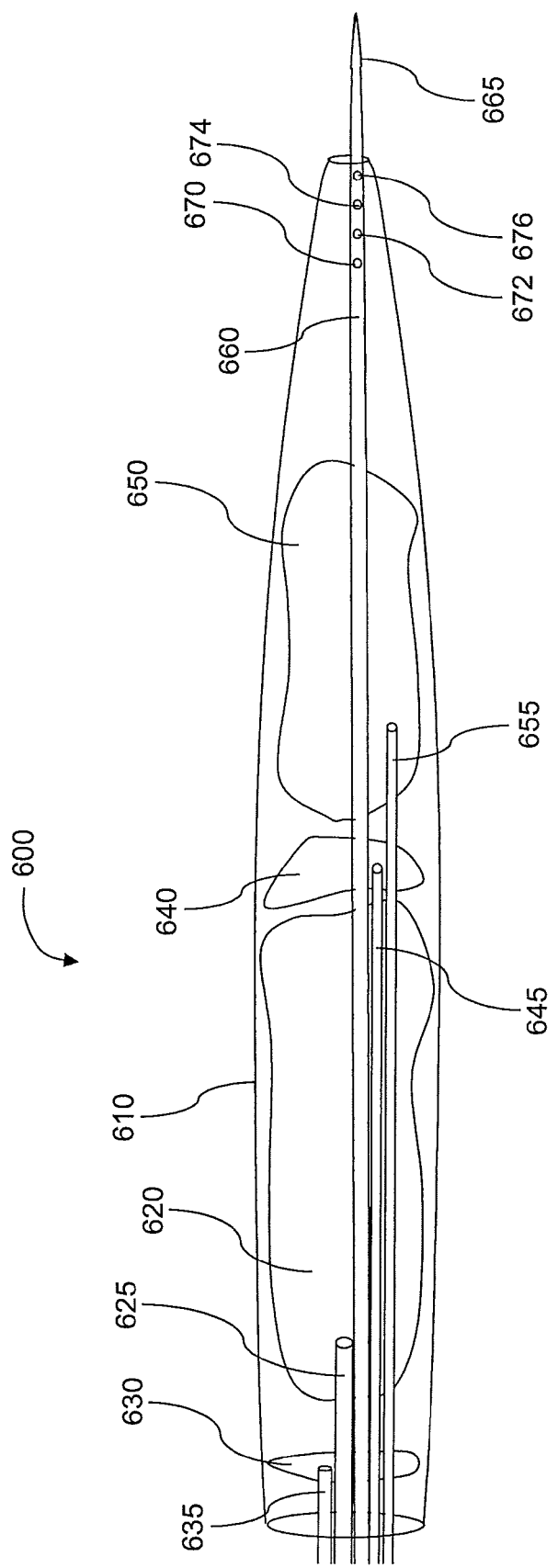
FIG. 9 is a depiction of a device in accordance with some embodiments described herein.

FIG. 9 depicts another embodiment of a device as provided herein. Device 600 can have elongate sheath 610 which, prior to insertion and deployment of device 600 into a patient, can contain gastric balloon 620, at least one gastric bumper balloon (e.g., gastric bumper balloon 630), pyloric balloon 640, duodenal balloon 650, and jejunal extension tube 660. The interior of each of balloons 620, 630, 640, and 650 can be in fluid communication with the lumens of tubes 625, 635, 645, and 655, respectively, through which fluid can be passed into and/or out of balloons 620, 630, 640, and 650. As shown, jejunal extension tube 660 can have weighted distal tip 665, and can define feeding ports 670, 672, 674, and 676.

Figure 10:
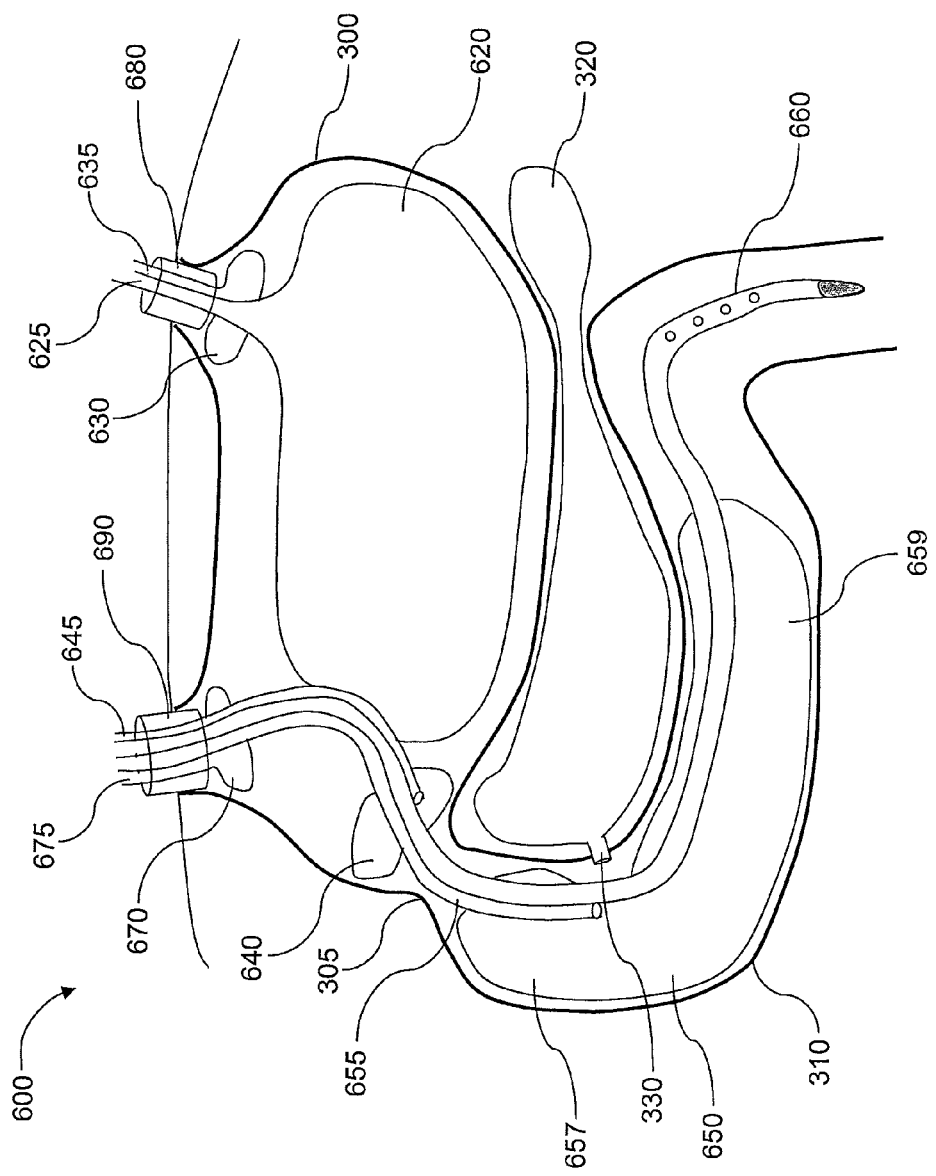
FIG. 10 is a depiction of a device in accordance with some embodiments described herein, placed in the digestive tract.

FIG. 10 is a depiction of device 600 placed percutaneously in a patient. Gastric balloon 620 and a first gastric bumper balloon (e.g., gastric bumper balloon 630) can be placed in stomach 300 via a first PEG Tubes 625 and 635 can be connected to balloons 620 and 630 such that the lumens of tubes 625 and 635 are in fluid communication with the interiors of balloons 620 and 630, respectively. Fluid can be passed into and/or out of balloons 620 and 630 via tubes 625 and 635. When first gastric bumper balloon 630 is inflated, it can help to retain gastric balloon 620 in stomach 300, such that gastric balloon 620 cannot be pulled out of stomach 300 until gastric bumper balloon 630 is deflated.

Device 600 also can include second gastric bumper balloon 670, in addition to pyloric retention balloon 640, duodenal balloon 650, and jejunal extension tube 660. The interiors of balloons 640, 650, 660, and 670 can be in fluid communication with the lumens of tubes 645, 655, 665, and 675, through which fluid can be passed into and/or out of balloons 640, 650, 660, and 670, respectively. Pyloric balloon 640, when positioned at or near pylorus 305 and inflated, can retain device 600 in position within stomach 300 and duodenum 310 of a patient. In some embodiments, duodenal balloon 650 can include proximal portion 657 and distal portion 659, and can be configured such that duodenal balloon 650 defines a space for ampulla of Vater 330.

Placement of device 600 in a patient via two separate PEG procedures can serve to orient gastric balloon 620 longitudinally and keep it positioned against the posterior wall of stomach 300, adjacent to pancreas 320. To place device 600 into a patient as depicted in FIG. 10, a first PEG procedure can be used to created first opening 680 in the more proximal stomach. Device 600 can be placed into the stomach through first opening 680. A scope then can be passed into the stomach through the mouth, and a second PEG procedure can be used to create second opening 690 in the more distal stomach. The portions of device 600 to be placed in the duodenum and jejunum then can be put into position. Sheath 610 device 600 can be removed. A smaller scope (e.g., a 6 mm "baby" scope) can be passed through second opening 690, and the proximal portions of tubes 645, 655, 665, and 675 can be grabbed with a forceps and externalized through second opening 690.

It is noted that any of the features described herein can be combined. For example, a device configured for percutaneous placement can include a pre-pyloric retention balloon with or without a "bumper" balloon. In addition, a device configured for oral or nasal placement can include a radio-opaque marker, with or without a pre-pyloric retention balloon and/or a post-esophageal retention balloon. The invention will be further described in the following examples, which do not limit the scope of the invention described in the claims.

EXAMPLES

To assess the localized cooling provided to the pancreas by devices as described herein, and to evaluate their effectiveness for alleviating conditions such as SAP, experiments such as those described below can be conducted.

In Vitro Studies on the Effect of Hypothermia in Pancreatitis:

The methods and endpoints discussed herein are used to determine the therapeutic effects of hypothermia. In addition, these are used to identify the optimum pancreatic temperature to be targeted by gastric balloon cooling devices.

Intra-cellular activation of trypsinogen to trypsin, which is dependent on cathepsin B, is an important mechanism in several models of pancreatitis (Singh et al. (2001a) *J. Clin. Invest.* 108:1387-1395). Prevention of trypsinogen activation results in reduced severity of pancreatitis. Since hypothermia reduces both the activity of trypsin and cathepsin B, the temperature range at which trypsin and cathepsin B activities are inhibited in acinar cells in vitro is evaluated and used for in vivo studies with the devices.

Both apoptotic and necrotic modes of cell death occur in pancreatitis (Singh et al. (2009, in press) *Am. J Physiol.*). Cell death in pancreatitis eventually leads to necrotizing pancreatitis and the complication of infected necrosis, which contributes to late mortality. Since hypothermia reduces both apoptotic and necrotic cell death in other systems (e.g., liver and brain), the temperature range at which apoptotic and necrotic cell death is inhibited in acinar cells in vitro is evaluated and used for in vivo studies with the devices.

Cytokines and proteases released by the pancreas contribute to the systemic inflammatory response and multi system organ failure associated with pancreatitis. Pancreatic acinar cells, which are the initiators of pancreatitis, generate cytokines and chemokines when exposed to stimuli that cause pancreatitis. Since hypothermia reduces the generation of cytokines and chemokines in other systems, the temperature range at which cytokine and chemokine generation is inhibited in vitro is evaluated and used for in vivo studies with the devices.

Acinar Preparation:

Intra-acinar phenomena are studied in vitro in primary acinar cells harvested from rats or mice (Singh et al. (2001a), supra; and Singh et al. (2009), supra). The quality of acinar cell preparations is confirmed by trypan blue exclusion, and generally is at least 95%.

Acinar Culture:

As previously (Sing et al. (2009), supra; and Singh and McNiven (2008) *Mol. Biol. Cell* 19:2339-2347), culture is carried out overnight in RPMI1640 with 10% fetal calf serum.

Stimuli to Induce Acinar Cell Injury and Inflammatory Mediator Generation:

The stimuli used are those that induce pancreatitis and cause trypsin generation in vitro, including Caerulein (100 nM), either alone or with 35 mM ethanol (as shown by Lu et al. (2002) *Am. J. Physiol. Gastrointest. Liver Physiol.* 282:G501-507), bile acids (0.45 mM), taurolithocholic acid 3-sulfate disodium salt (TLCS), 1.2 mM taurochenodeoxycholate (TCDC; Fischer et al. (2007) *Am. J. Physiol.* 292: G875-886).

Induction of Hypothermia:

The effect of hypothermia is initially tested prophylactically (i.e., initiated before the stimulus and maintained during contact with the stimulus) at the temperatures mentioned below. To test therapeutic effects, after different periods (e.g., 1, 3, 10, 20, or 50 minutes) of exposure to the stimulus at 37° C., the original medium is replaced by new media containing the stimulus and incubating cells at the desired temperature (e.g., 32° C., 27° C., 22° C., 17° C., or 12° C.). While 32° C. and 27° C. can be achieved in a $CO_2$ incubator, the lower temperatures likely require placing a cooling bath in the incubator. At the end of incubation, all reactions are stopped on ice and samples are processed as described previously (Singh et al. (2009), supra; Singh and McNiven, supra; Singh et al. (2001a), supra; and Singh et al. (2001b) *Gastroenterol.* 120:1818-1827).

Temperature of Significant Inhibition:

This term refers to the highest temperature inhibiting an outcome (e.g., trypsin generation) by 80% of that induced at 37° C. Separate temperatures are determined for prophylaxis (Tp) and for each therapeutic time point (Tt). The "TTt" represents the "latest time point-highest temperature" at which 80% inhibition occurs in the therapeutic setting. Comparing Tp with the temperature of TTt gives the temperature range over which a deleterious outcome (e.g., cell death) is inhibited. The TTt is determined for cell death and inflammatory mediator generation. A very low Tp suggests a phenomenon's resistance to hypothermia.

Statistics:

All in vitro experiments are done in duplicates and repeated a minimum of three times, and values are reported as mean±SEM. Statistical significance between two groups is evaluated by student's t test, and for more than two groups is evaluated by analysis of variance (ANOVA). If ANOVA indicates a significant difference, the data are analyzed using Turkey's method as a post hoc test for the difference between groups. A p value<0.05 is considered significant. For in vivo imaging studies, pathology is conducted in a blinded fashion.

Determination of the Temperature Range Over which Cell Death Phenomena and Inflammatory Mediator Generation are Inhibited:

The effect of graded hypothermia on intra-acinar trypsin generation is evaluated. The stimuli described above cause trypsin activity to peak at 37° C. in 30-60 minutes. Trypsin activity is assayed at 37° C., and individual thermal profiles for pancreatic cathepsin B and trypsin also are studied using their individual substrates. The Tp and TTt for trypsin generation are determined as described herein.

The effect of graded hypothermia on activities of enzymes active in pancreatitis was examined, using protocols as discussed above. Data are presented in Table 2.

TABLE 2

Effect of graded hypothermia on activities of enzymes active in pancreatitis

| | Bovine trypsin | | Human cathepsin B | |
|---|---|---|---|---|
| temperature | activity | % max 37° C. | activity | % max 37° C. |
| 37° C. | 3036 | 100 | 2000 | 100 |
| 33° C. | ND | ND | 1646 | 82.3 |
| 30° C. | ND | ND | 1498 | 74.9 |
| 23° C. | 1616 | 53.2 | 1271 | 63.6 |
| 4° C. | 781 | 25.7 | 522 | 26.1 |

ND: Not done.
Results are from a single experiment. All activities were tested at least in duplicate.

Cathepsin B generates trypsin by cleaving the trypsin precursor, trypsinogen. Cooling to a temperature that would slow both (e.g., 23° C., which slowed both trypsin and cathepsin B by about 50%) should result in a synergistic reduction (e.g., to about 25%) if trypsinogen and cathepsin B are combined and trypsin activity is measured. Experiments to test this hypothesis revealed that cathepsin B-mediated trypsinogen activation at 23° C. was 27% of the level observed at 37° C.

If hypothermia reduces trypsin generation, studies on the effect of hypothermia on "co-localization" of cathepsin B with zymogens are conducted (Singh et al. (2001a), supra). A Tp lower than is biologically feasible in vivo, pharmacologic inhibitors (e.g., CA-074me (Van Acker et al. (2002) *Am. J. Physiol.* 283:G794-800) or Gabexate mesylate (Buehler et al. (1993) *Gastroenterol.* 104:1165-1170), both of which have been used in vivo) are combined with hypothermia and the effects of hypothermia on upstream Class III PI-3 kinases (Singh et al. (2001a), supra) and calcium signaling are examined.

Studies are conducted to assess how graded hypothermia affects acinar cell death. The stimuli and conditions for these are described herein, and the time points are 15 minutes, 45 minutes, 2 hours, and 4 hours. Further time points can be used to achieve significant cell death (>50% cells) for a particular stimulus. Hypothermia is induced initially prophylactically, and then after 3, 10, 30, or 90 minutes. The later time points are included to study whether cell death is reduced even if upstream signaling has been initiated. The Tp for each phenomenon and TTt (for LDH leakage, Hoechst dye nuclear incorporation, annexin V staining) are determined as described herein.

Measures of cell death are determined as percentage of total LDH leakage in serum free medium (kit from Sigma-Aldrich), as previously measured (Singh et al. (2001b), supra), and by Hoechst dye nuclear incorporation (8 mg/ml Hoechst 33342 added for 15 minutes after treatment, and imaged with a LSM 510 confocal microscope). Apoptotic cells exhibit fragmented or condensed nuclei, whereas necrotic cells may not have significant nuclear changes or may have slightly swollen nuclei. Results are reported as % of cells with given nuclear changes.

Annexin V staining (ApoAlert Annexin V FITC Apoptosis Kit, Clontech) is used to measure apoptosis. Cells are counter-stained with propidium Iodide (PI) (1 µM) to stain necrotic cells and imaged using dual fluorescence as described previously (Singh and McNiven, supra). Apoptotic cells are Annexin V positive and PI negative. PI positive cells are counted as late apoptosis or necrosis. The effect of graded hypothermia on generic reduction in cell death is measured, as is the conversion of one mode of cell death to another (e.g., necrotic to apoptotic).

Acinar ATP levels under these conditions are measured as previously described (Sing et al. (2001b), supra). Decreased ATP levels can suggest necrotic cell death. These are correlated with apoptotic vs. necrotic outcomes, in addition to serving as a control for physiological processes.

Studies on the effect of hypothermia on upstream signaling resulting in cell death (e.g., mitochondrial depolarization (Singh et al. (2009), supra)) using JC-1 can be planned. Effects on apoptotic outcomes may be verified by measuring active caspase-3 using Ac-DEVD-AMC and western blotting (Gukovskaya et al. (2006) *J. Gastroenterol. Hepatol.* 21 Suppl. 3:S10-13). A Tp lower than what is biologically feasible in vivo results in that mode of cell death being termed resistant to hypothermia.

The effects of hypothermia on upstream phenomena (e.g. blebbing (Singh and McNiven, supra) and mitochondrial depolarization (Singh et al. (2009), supra)) are evaluated, and pharmacologic inhibition of these phenomena (e.g., with Dasatinib or Nelfinavir) are is combined with hypothermia if necessary.

The effect of hypothermia on generation of inflammatory mediators is studied using conditions as described above and previously (Singh et al. (2009), supra). TNF-α (200 ng/ml), which activates NF-κB in acinar cells, is used in addition to other stimuli as described herein.

Up-regulation of the mRNA for the cytokine TNF-α and the CXC-ELR chemokine keratinocyte cytokine (KC, the murine equivalent of human IL-8; Singh et al. (2009), supra) with 100 nM Caerulein (CER) are compared to controls. This does not occur with physiologic caerulein (0.1 nM).

Temperature dependence of these phenomena is studied using previously described conditions (Singh et al. (2009), supra). Briefly, after overnight culture, graded hypothermia is induced, initially prophylactically and then after different periods (e.g., 1, 3, 10, 20, and 40 minutes) of incubation at 37° C. Samples are suspended in RNALater (Ambion, Austin, Tex.), and RNA is extracted (Totally RNA, Ambion) and reverse transcribed. PCR products using 18S internal standards with TNF-α, KC specific primers are analyzed on a 1% agarose gel with Cyber Gold (BioWhittaker, Walkersville, Md.) and quantified (Gel Doc, Hercules, Calif.). Results are verified using real time PCR (Applied Biosystems, Foster City, Calif.). The Tp and TTt are determined.

A Tp lower than is biologically feasible in vivo will result in the inflammatory mediator generation being deemed resistant to hypothermia. Studies of the effect of hypothermia on upstream phenomena (e.g., NF-κB activation, Singh et al. (2007) *Gut* 56:958-964), calcium and PKC signaling, and pharmacologic inhibition of these (e.g., with N-Acetyl cysteine, which is used in humans) is combined with hypothermia if necessary.

In Vivo Studies:

Gastric balloon devices are used to attain pancreatic temperatures in the Tp to TTt range, aiming for the highest TTt that inhibits both cell death and inflammatory mediator generation. The in vivo studies are done in two stages. First, conditions to attain TTt in the pancreas with the device are optimized, and its safety is tested. Second, the efficacy of the device in animal models of pancreatitis is evaluated.

Placement and Optimization of Device in Rats:

250 g fasted male Wistar rats are anesthetized (e.g., with 100 mg/kg ketamine IP and 15 mg/kg xylaxine IP) and placed on a heated table with a rectal temperature probe. With sterile precautions and antibiotics (e.g., cefazolin, 100 mg/kg IM), an upper midline incision is made and a purse string suture is placed on the anterior stomach wall (5/0 silk). The stomach is cleared of debris through an opening therein. Two sterile polyethylene catheters (inflow and outflow) with a 3 mm internal diameter, covered by a sterile latex balloon (4 ml volume at 30 cm water pressure) are inserted and the tubing is fixed by closing the purse string suture. A Thermocouple Flexible Implantable Probe (Cat No. 521732, Harvard Apparatus), is placed on the posterior pancreatic body surface to monitor the temperature. The incision is closed, and the catheters and thermocouple probes are tunneled subcutaneously to the back of the neck and connected to their respective devices. Analgesic buprinorphine is given (0.05 mg/kg, repeated Q 8 hourly). The rats are placed in a jacket. The inflow tubing is connected through a peristaltic pump (flow rate up to 1 to 25 ml/minute) to a 4° C. cooling reservoir. The stomach outflow is returned to the reservoir.

Animals are kept warm and allowed to recover. The height of the cooling reservoir is such that stomach volume sufficient to make contact with the pancreas (confirmed on ultrasound) is achieved. Both rectal and pancreatic temperatures are monitored, and pancreatic temperature is adjusted by regulating the flow rate of the liquid from the reservoir.

Initially flow rates are low (3 ml/minute for rats), and adjusted until the chosen TTt is reached in the pancreas. The flow rates and height of reservoir are noted and used for future reference. The animals are monitored for the duration of the intended local hypothermia (i.e., 24 hours). This includes rectal temperatures, other vitals, pain and feeding behavior, blood glucose Q 12 hourly, infectious complications, and FDG uptake in the pancreas studied by PET.

Placement and Optimization of the Device in Domestic Farm Pigs:

Pigs (30-40 kg) are sedated (ketamine) and endotracheally intubated for the surgical procedure. Inhalation anesthesia (halothane) is used. Pancreatic and rectal thermocouples are placed as above. A gastric balloon (800 ml) with a jejunal extension is placed by percutaneous endoscopic gastrostomy (PEG). The device is secured with a jacket and connected to a steel hose through which the tubing passes.

Animals are kept warm and allowed to recover. The 4° C. cooling reservoir's height is such that stomach volume is sufficient to make contact with the pancreas (confirmed on ultrasound). Both rectal and pancreatic temperatures are monitored, and the temperature of the pancreas is adjusted by regulating the flow rate.

Flow rates initially are low (100 ml/minute), and are adjusted until the chosen TTt is reached in the pancreas. The flow rates and height of reservoir are noted and used for future reference. The animals are monitored for the duration of the intended local hypothermia (i.e., 7 days). This includes rectal temperatures, other vitals, pain and feeding behavior, blood glucose Q 12 hourly, and infectious complications.

The flow rates also provide an option to study the association of pancreatic temperature attained with body weight/lean mass, and to assess whether there is a variation with species (e.g., rats vs. pigs). This can provide guidance about suitable flow rates for use in humans. In addition, flow rates and temperatures are correlated with the SUVs noted at the time of PET (vs. controls, i.e., no cooling device).

Standardize the Safety of the Device:

The purpose of inducing local hypothermia with the device is to avoid the complications of generalized hypothermia. Potential complications of local hypothermia of the pancreas through the stomach include gastric ischemia/pressure effects, pancreatic exocrine and endocrine dysfunction, intolerance to enteral feeding, and mechanical complications including burst balloons, kinking of the hose, and displacement of the device. These issues are addressed as follows.

1) Generalized hypothermia is prevented by monitoring body temperature at a distant site (rectal or tympanic), using warming blankets, and adjusting the temperature of the environment. Vitals signs are monitored Q12 hourly. In case TTt results in a drop in body temperature, the highest Tp is used. This is a reasonable option since pancreatic injury progresses over days in humans.

2) Although unlikely, potential compromise of supportive systems [e.g., cardiovascular (cardiac output, blood pressure, heart rate), lungs (pulseoximetry, respiratory rate), and renal (BUN, creatinine)] are closely monitored.

3) At the time of necropsy, stomach mucosa are e examined grossly and histologically for gastric injury.

4) Compromise of physiologic pancreatic functions due to hypothermia is prevented as follows. Endocrine insufficiency is detected in the preliminary experiments and blood glucose levels are monitored Q12 hourly. Animals are given insulin on an as-needed basis. For exocrine insufficiency, Peptamen (elemental nutrition) is given in pigs. Exocrine loss is inconsequential in the rat models.

5) Tolerance to enteral feeding assessed by monitoring oral intake. If oral intake is decreased, naso jejunal supplementation is increased. Weight gain also is monitored.

6) Mechanical complications are monitored and corrected on an as-needed basis.

The therapeutic efficacy of the device in animal models of pancreatitis is evaluated using three models: (a) a caerulein (mild, short duration) model in rats; (b) taurocholate (severe, short duration) models in rats; and (c) a taurocholate model in pig (severe, long duration).

The rat models are used to test the device's ability to speedily cool and slow down pancreatitis (on PET scan) in rapidly evolving (6-24 hours) models. Both mild and severe models are used since the clinical course in humans cannot be predicted using the current tools. The pig model replicates human biliary pancreatitis, and is studied with tools used in human pancreatitis (e.g., CT with IV contrast). For each model, there are four groups (eight animals per group). These are controls (no pancreatitis), pancreatitis, pancreatitis with local hypothermia, and pancreatitis with placement of the balloon but no hypothermia.

Methods:

The rat models of pancreatitis are set up as described previously (Singh and McNiven, supra; and Singh et al. (2001a), supra). The timing of hypothermia is as described in Table 3. The pig model, is used as described previously but with the following modifications. The pancreatic duct is ligated and connected to a refillable series 2500 subcutaneous implanted pump (Harvard Apparatus Cat. #724605) with a 3 French silicone catheter. Sodium taurocholate (5%) is administered at 1 ml/kg over 24 hours to simulate human disease. The timing of hypothermia is as described in Table 3. The catheter is put to gravity drainage after three days. Both groups (i.e., with and without hypothermia) with tubes are fed Peptamen jejunally. Maintenance fluids (40 ml/kg/24 hours) are given to all animals to maintain hydration.

TABLE 3

|  | CER (8 rats/group) | TAUR (8 rats/group) | Pig (8 pigs/group) |
|---|---|---|---|
| Induce pancreatitis | 0 hrs. | 0 hrs. | 0 hrs. |
| Induce hypothermia | 1 hr. | 2 hrs. | 24 hrs. |
| Give FDG* or IV contrast** | 3 hrs. | 4 hrs. | 24 hrs. |
| Do PET* or CT** | 3.5 hrs. | 4.5 hrs. | 24 hrs. |
| Sacrifice* | 6 hrs. | 24 hrs. | N/A |
| Drain obstruction** | N/D | N/D | 3 d |
| Do contrast CT** | N/D | N/D | 8 d |
| Stop hypothermia** | N/D | N/D | 8 d |
| Do contrast CT, sacrifice** | N/A | N/A | 8 d |

*= rat groups only;
**= pig group only;
N/A = not applicable;
N/D = not done

The decrease in the pancreas' metabolic demand with the cooling device is determined using PET during pancreatitis. This is determined in rats for the following reasons: (1) There is no accurate tool to predict severity in humans with pancreatitis, and thus the device is likely to be placed in both mild and severe pancreatitis. The efficacy of the device to decrease the metabolic demand is thus tested in both mild (caerulein) and severe (taurocholate) pancreatitis. (2) The rapid onset (within a few hours) of both mild (caerulein) and severe (taurocholate) pancreatitis in rats will allow assessment of how rapidly the device can reverse these diseases. (3) The efficacy in reducing FDG uptake is correlated with the outcome in local and systemic injury at the time of necropsy. (4) The weight limit of the available PET scanner prevents study of pigs by this method.

For the caerulein model, the device and thermocouple in the pancreatic bed are placed the evening before, and animals are allowed to recover. Pancreatitis is induced the next morning with caerulein (20 μg/kg, IP). As shown in Table 3, hypothermia is induced one hour later. Two hours after this, the animals are given FDG and imaged at 3.5 hours from the onset of pancreatitis. Individual SUVs for the different groups are measured by PET in a blinded fashion and compared at the end of the study. The animals are sacrificed at six hours and the effect of local hypothermia on local pancreatic injury are compared between groups. This includes edema (measured as percentage water content), trypsin activity, apoptosis (TUNELS, active caspase-3 staining and activity), histology, myeloperoxidase activity (neutrophil infiltration) and local cytokine generation (TNF-α and KC). There is no systemic injury in this model.

In the taurocholate model, the gastric balloon device and pancreatic thermocouple are placed at the time of induction of pancreatitis (5% sodium taurocholate, administered intraductally at 1 mg/kg over 5 minutes). Hypothermia is induced two hours after the onset of pancreatitis (Table 3). FDG is given at four hours, and the animals are imaged by PET at 4.5 hours. Individual SUVs for the different groups are measured in a blinded fashion and compared at the end of the study. The animals are sacrificed at 24 hours and the effect of local hypothermia on local pancreatic injury are compared between groups. This includes edema (measured as percentage water content), trypsin activity, apoptosis (TUNELS, active caspase-3 staining and activity), necrosis (hematoxylin and eosin staining), myeloperoxidase activity (neutrophil infiltration), and local cytokine generation (TNF-α and KC). Systemic inflammatory mediator levels (IL-8, TNF-α, MIP-2, IL-6, MCP-1) and CRP levels are measured. Lung injury is assessed by myeloperoxidase levels and histology.

The therapeutic effects of the devices on local pancreatic injury are determined in a model similar to human disease. The pig model is used to look at the long term protective effect of the device on progression of damage over a week, and also on recovery after stopping hypothermia at eight days—with the animals being observed until 14 days. CT with IV contrast as in humans is done on days 1, 7, and 14 to determine the amount of pancreas with "necrosis" (Table 3). Markers of injury, i.e., edema, histology, mechanism of cell death, and trypsin are studied on harvested pancreas. Inflammatory markers, i.e., myeloperoxidase (for neutrophil infiltration) will be measured (Singh et al. (2009), supra) and CD3 (T cell), CD20 (B cell), CD33 (monocyte) are stained on cryosections.

The therapeutic effect of localized hypothermia induced with devices as described herein is determined with respect to systemic injury. These studies are conducted to test the hypothesis that blunting local injury without compromising supportive systems (respiratory, circulatory, renal) reduces systemic injury. This initially manifests as Systemic inflammatory response syndrome (SIRS) with tachycardia, rise or drop in body temperature, white count and drop in oxygenation or tachypnea. It goes on to lung injury, shock and renal failure.

SIRS are assessed with vitals and complete blood count (CBC) at 24 hour intervals, along with IL-8, TNF-α, MIP-2, IL-6, MCP-1, and CRP. Lung injury is studied by pulse oximetery, lung histology, and myeloperoxidase (Singh et al. (2009), supra). BAL fluids, lactate dehydrogenase (LDH) levels, and leakage of FITC albumin given IV two hours before necropsy from the vascular space into the alveolar space. Shock is monitored by measuring blood pressure in pigs. Maintenance fluids as mentioned before are given. Renal failure is monitored by measuring the blood urea nitrogen (BUN) and serum creatinine.

There are measures to strengthen the potential weaknesses associated with these methods.

1) Choosing between two different TTt (e.g., cell death and inflammation): To prevent both phenomena, the lower TTt is chosen. Tp is predicted to be the highest temperature of significant inhibition.

2) If one TTt is lower than feasible in vivo there are two lines of action: first, the Tp is chosen (since pancreatic necrosis is a process that progresses over days, and injury to the remaining pancreas may be prevented). If the Tp also is too low, the methods may include: ii) Combine pharmacologic inhibition with hypothermia to target the evading mechanism (e.g., N-acetyl cysteine for transcription factors, nelfinavir for cell death (Singh et al. (2009), supra), Gabexate or Ca-074 me for trypsin (Buehler et al., supra; and Van Acker et al., supra) for trypsin, Dasatinib for blebbing (Singh and McNiven, supra; these have been used in humans or experimental pancreatitis) and studying it as a separate group in vivo.

3) Duration of induction of hypothermia: This cannot be indefinite, and is seven of the 14 study days planned.

4) Need for removing insult causing pancreatitis: Hypothermia alone can slow down deleterious processes locally but may not remove the insult such as an obstructing gall stone, necessitating need for therapeutic intervention—e.g., relieving an obstruction. Therefore the pancreatic duct catheter will be put to free drainage three days after inducing pancreatitis.

5) The time intervals after the stimuli in vitro are short, but they are relevant both to the models and clinically, since local pancreatic damage is a process that progresses over days and there may be normal pancreas at the time of clinical presentation (days 1 and 2) that becomes damaged later in the study (days 5-7).

6) Assessing affect of hypothermia on inflammatory or other cells involved in pancreatitis: This has been done previously. In vivo models measure the actual outcome.

7) Mechanical complications: These are monitored and corrected. Pigs are in a swine jacket.

8) Long term detrimental effects of hypothermia: these are extremely unlikely, since after incubation at 4° C. for 72 hours, the pancreas has full gain of exocrine and endocrine function.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A device comprising a hollow balloon catheter having a plurality of balloons thereon, wherein at least one of said plurality of balloons is configured for placement in the stomach of a patient, wherein two said plurality of balloons are configured for placement in the duodenum of said patient such that there is a space for the ampulla of Vater, and wherein said device further comprises a distal portion configured for placement in the jejunum of said patient, said distal portion defining one or more ports such that the interior of said device is in fluid communication with the interior of said jejunum.

2. The device of claim 1, wherein said balloon catheter comprises a proximal end with a nasal placement member that permits said balloon catheter to pass through a nostril of said patient.

3. The device of claim 1, further comprising a radio-opaque marker.

4. The device of claim 3, wherein said radio-opaque marker is located distal to said at least one balloon configured for placement in the stomach and proximal to said balloons configured for placement in the duodenum.

5. The device of claim 3, wherein said radio-opaque marker is located on a portion of said balloon configured for placement in the stomach, wherein said portion is adapted to be positioned toward the posterior portion of the stomach.

6. The device of claim 1, comprising two balloons configured for placement in the stomach of said patient.

7. The device of claim 1, wherein said at least one balloon configured for placement in the stomach comprises two or more chambers.

8. The device of claim 7, wherein at least one of said chambers is adapted to be positioned toward the posterior portion of the stomach, and wherein another of said chambers is adapted to be positioned toward the anterior portion of the stomach.

9. The device of claim 7, wherein each of said two or more chambers has an interior in fluid communication with the lumen of one or more hollow connectors.

10. A gastroduodenal device comprising:
   a balloon catheter comprising a proximal end and a distal end;
   a gastric balloon attached to and located along the hollow balloon catheter between the proximal end and the distal end of the balloon catheter;
   a first duodenal balloon attached to and located along the balloon catheter between the gastric balloon and the distal end of the balloon catheter, wherein the first duodenal balloon is spaced from the gastric balloon along the balloon catheter by a first distance configured to place the first duodenal balloon in the duodenum of a patient distal from the ampulla of Vater of the patient when the gastric balloon is in the stomach of the patient;
   a second duodenal balloon attached to and located along the balloon catheter between the gastric balloon and the first duodenal balloon, wherein the second duodenal balloon is spaced from the first duodenal balloon along the balloon catheter by a second distance, wherein the second distance is configured to place the second duodenal balloon in the duodenum proximal of the ampulla of Vater when the first duodenal balloon is distal from the ampulla of Vater in the duodenum and the gastric balloon is in the stomach of the patient;
   a first duodenal balloon lumen passing through the balloon catheter and in fluid communication with the first duodenal balloon, wherein the first duodenal balloon lumen is configured to deliver first duodenal balloon cooling fluid to the first duodenal balloon;
   a second duodenal balloon lumen passing through the balloon catheter and in fluid communication with the second duodenal balloon, wherein the second duodenal balloon lumen is configured to deliver second duodenal balloon cooling fluid to the second duodenal balloon; and
   a jejunal extension tube passing through the balloon catheter, wherein the jejunal extension tube extends to a port located distal of the first duodenal balloon, wherein the jejunal extension tube is configured to deliver nutrients directly into the jejunum of the patient when the gastric balloon is located in the stomach and the first and second duodenal balloons are located in the duodenum of the patient.

11. The device of claim 10, wherein the gastric balloon further comprises a posterior chamber and an anterior chamber, and wherein the device further comprises a posterior chamber lumen in fluid communication with the posterior chamber and an anterior chamber lumen in fluid communication with the anterior chamber, wherein the posterior chamber lumen is configured to deliver gastric balloon cooling fluid to the posterior chamber of the gastric balloon.

12. The device of claim 11, wherein the gastric balloon comprises a radio-opaque marker, wherein the radio-opaque marker is configured such that the posterior chamber is positioned adjacent the pancreas when the radio-opaque marker is positioned adjacent the pancreas.

13. The device of claim 10, wherein the gastric balloon comprises a weighted distal end, wherein the weighted distal end comprises a portion of the gastric balloon closest to the first duodenal balloon.

14. The device of claim 10, wherein the proximal end of the balloon catheter comprises a nasal placement member configured to permit the balloon catheter to pass through a nostril of the patient.

15. The device of claim 10, wherein the device further comprises a first gastric bumper balloon attached to and located on the balloon catheter between the gastric balloon and the proximal end of the balloon catheter, wherein the first gastric bumper balloon is configured for placement in the stomach of the patient, and wherein the location of the first gastric bumper balloon on the balloon catheter is configured to position the gastric balloon in the stomach for placement in the stomach of the patient, and wherein the location of the first gastric bumper balloon on the balloon catheter is configured to position the gastric balloon in the stomach.

16. The device of claim 15, wherein the location of the first gastric bumper balloon on the balloon catheter is further configured to position the first duodenal balloon in the duodenum distal from the ampulla of Vater and the second duodenal balloon in the duodenum proximal of the ampulla of Vater when the first gastric bumper balloon is located against a wall of the stomach.

17. The device of claim 15, wherein the first gastric bumper balloon is further configured to resist removal of the gastric balloon from the stomach when the first gastric bumper balloon is inflated.

18. The device of claim 15, wherein the device further comprises a second gastric bumper balloon attached to and located on the balloon catheter between the gastric balloon and the second duodenal balloon, wherein the second gastric bumper balloon is configured for placement in the stomach of the patient, and wherein the location of the second gastric bumper balloon on the balloon catheter is configured to position the gastric balloon in the stomach.

* * * * *